US010325686B2

(12) United States Patent
Mansi et al.

(10) Patent No.: US 10,325,686 B2
(45) Date of Patent: Jun. 18, 2019

(54) SYSTEM AND METHODS FOR INTEGRATED AND PREDICTIVE ANALYSIS OF MOLECULAR, IMAGING, AND CLINICAL DATA FOR PATIENT-SPECIFIC MANAGEMENT OF DISEASES

(71) Applicants: Tommaso Mansi, Westfield, NJ (US); Wei Keat Lim, Jersey City, NJ (US); Vanessa King, Princeton, NJ (US); Andreas Kremer, Vienna (AT); Bogdan Georgescu, Plainsboro, NJ (US); Xudong Zheng, Plainsboro, NJ (US); Ali Kamen, Skillman, NJ (US); Andreas Keller, Püttlingen (DE); Cord Friedrich Staehler, Hirschberg an der Bergstrasse (DE); Emil Wirsz, Fürth (DE); Dorin Comaniciu, Princeton Junction, NJ (US)

(72) Inventors: Tommaso Mansi, Westfield, NJ (US); Wei Keat Lim, Jersey City, NJ (US); Vanessa King, Princeton, NJ (US); Andreas Kremer, Vienna (AT); Bogdan Georgescu, Plainsboro, NJ (US); Xudong Zheng, Plainsboro, NJ (US); Ali Kamen, Skillman, NJ (US); Andreas Keller, Püttlingen (DE); Cord Friedrich Staehler, Hirschberg an der Bergstrasse (DE); Emil Wirsz, Fürth (DE); Dorin Comaniciu, Princeton Junction, NJ (US)

(73) Assignees: Siemens Healthcare GmbH, Erlangen (DE); SIEMENS AG OSTERREICH, Vienna (AT)

( * ) Notice: Subject to any disclaimer, the term of this patent is extended or adjusted under 35 U.S.C. 154(b) by 604 days.

(21) Appl. No.: 13/928,430

(22) Filed: Jun. 27, 2013

(65) Prior Publication Data
US 2014/0012558 A1 Jan. 9, 2014

Related U.S. Application Data

(60) Provisional application No. 61/668,201, filed on Jul. 5, 2012.

(51) Int. Cl.
G16H 50/50 (2018.01)
G16B 5/00 (2019.01)

(52) U.S. Cl.
CPC ............. G16H 50/50 (2018.01); G16B 5/00 (2019.02)

(58) Field of Classification Search
None
See application file for complete search history.

(56) References Cited

U.S. PATENT DOCUMENTS 9,129,053 B2 9/2015 Mansi et al.
2007/0130206 A1 7/2007 Chakraborty
2011/0112808 A1 12/2011 Fonss Nielsen
2013/0226542 A1 8/2013 Rapaka et al.

FOREIGN PATENT DOCUMENTS

CN 101330867 A 12/2008
WO 0157775 A2 9/2001

OTHER PUBLICATIONS

PCT International Search Report dated Jan. 17, 2014 corresponding to PCT International Application No. PCT/US2013/049205 filed Jul. 3, 2013 (14 pages).
Multiscale Modeling: Physiome Project Standards, Tools and Databases Peter J. Hunter, vol. 39, No. 11, Nov. 1, 2006.
Campbell, Stuart G., and Andrew D. McCulloch. "Multi-scale computational models of familial hypertrophic cardiomyopathy: genotype to phenotype." Journal of The Royal Society Interface 8.64 (2011): 1550-1561.
Campbell, Stuart G., et al. "Effect of transmurally heterogeneous myocyte excitation-contraction coupling on canine left ventricular electromechanics." Experimental physiology 94.5 (2009): 541-552.
Chapelle, Dominique, et al. "Energy-preserving muscle tissue model: formulation and compatible discretizations." International Journal for Multiscale Computational Engineering 10.2 (2012).
Clayton, R. H., et al. "Models of cardiac tissue electrophysiology: progress, challenges and open questions." Progress in biophysics and molecular biology 104.1-3 (2011): 22-48.
Costa, Kevin D., Jeffrey W. Holmes, and Andrew D. McCulloch. "Modelling cardiac mechanical properties in three dimensions." Philosophical transactions of the Royal Society of London. Series A: Mathematical, physical and engineering sciences 359.1783 (2001): 1233-1250.

(Continued)

Primary Examiner — G Steven Vanni

(57) ABSTRACT

A system operating in a plurality of modes to provide an integrated analysis of molecular data, imaging data, and clinical data associated with a patient includes a multi-scale model, a molecular model, and a linking component. The multi-scale model is configured to generate one or more estimated multi-scale parameters based on the clinical data and the imaging data when the system operates in a first mode, and generate a model of organ functionality based on one or more inferred multi-scale parameters when the system operates in a second mode. The molecular model is configured to generate one or more first molecular findings based on a molecular network analysis of the molecular data, wherein the molecular model is constrained by the estimated parameters when the system operates in the first mode. The linking component, which is operably coupled to the multi-scale model and the molecular model, is configured to transfer the estimated multi-scale parameters from the multi-scale model to the molecular model when the system operates in the first mode, and generate, using a machine learning process, the inferred multi-scale parameters based on the molecular findings when the system operates in the second mode.

11 Claims, 16 Drawing Sheets

(56) References Cited

OTHER PUBLICATIONS

Fuerst, Bernhard, et al. "A personalized biomechanical model for respiratory motion prediction." International Conference on Medical Image Computing and Computer-Assisted Intervention. Springer, Berlin, Heidelberg, 2012.

Georgescu, Bogdan, et al. "Database-guided segmentation of anatomical structures with complex appearance." 2005 IEEE Computer Society Conference on Computer Vision and Pattern Recognition (CVPR'05). vol. 2. IEEE, 2005.

Hunter, Peter J., and Thomas K. Borg. "Integration from proteins to organs: the Physiome Project." Nature reviews Molecular cell biology 4.3 (2003): 237.

Ionasec, Razvan Ioan, et al. "Patient-specific modeling and quantification of the aortic and mitral valves from 4-D cardiac CT and TEE." IEEE transactions on medical imaging 29.9 (2010): 1636-1651.

Kerckhoffs, Roy CP, et al. "Coupling of a 3D finite element model of cardiac ventricular mechanics to lumped systems models of the systemic and pulmonic circulation." Annals of biomedical engineering 35.1 (2007): 1-18.

Lin, Chen-Ching, et al. "Dynamic functional modules in co-expressed protein interaction networks of dilated cardiomyopathy." BMC systems biology 4.1 (2010): 138.

Lim, Wei Keat, Eugenia Lyashenko, and Andrea Califano. "Master regulators used as breast cancer metastasis classifier." Biocomputing 2009. 2009. 504-515.

Lim WK, Grady L. Molecular Network-based Method for Cardiomyopathy Classification; U.S. Appl. No. 61/593,899, filed Feb. 2, 2012.

Lim WK.; Method to Reverse Engineer Context-specific Gene Regulatory Network.; U.S. Appl. No. 61/606,516, filed Mar. 5, 2012.

Loader, Clive. Local regression and likelihood. Springer Science & Business Media, 2006.

Mansi, Tommaso, et al. "A statistical model for quantification and prediction of cardiac remodelling: Application to tetralogy of fallot." IEEE transactions on medical imaging 30.9 (2011): 1605-1616.

Tommaso Mansi, Bogdan Georgescu, Xudong Zheng, Ali Ka men, Dorin Comaniciu, System and Methods for Patient-Specific Planning of Cardiac Resynchronization Therapy based on Preoperative MRI or Ultrasound Data, Model Extension.

Tommaso Mansi, Viorel Mihalef, Xudong Zheng, Bogdan Georgescu, Saikiran Rapaka, Puneet Sharma, Ali Kamen, Dorin Comaniciu. A System and Method for Patient-Specific Planning and Simulation of Cardiac Therapy Based on Multi-Physics Fluid-Solid Heart Models from MRI or Ultrasound Images.

Marchesseau, Stéphanie, et al. "Fast porous visco-hyperelastic soft tissue model for surgery simulation: application to liver surgery." Progress in biophysics and molecular biology 103.2-3 (2010): 185-196.

Margolin, Adam A., et al. "Reverse engineering cellular networks." Nature protocols 1.2 (2006): 662.

Mitchell, Colleen C., and David G. Schaeffer. "A two-current model for the dynamics of cardiac membrane." Bulletin of mathematical biology 65.5 (2003): 767-793.

Noble, Denis. "A modification of the Hodgkin-Huxley equations applicable to Purkinje fibre action and pacemaker potentials." The Journal of physiology 160.2 (1962): 317-352.

Nordsletten, D. A., et al. "Coupling multi-physics models to cardiac mechanics." Progress in biophysics and molecular biology 104.1-3 (2011): 77-88.

O'Donnell, Thomas, et al. "Tracking and analysis of cine-delayed enhancement MR." International Conference on Medical Image Computing and Computer-Assisted Intervention. Springer, Berlin, Heidelberg, 2005.

Peyrat, Jean-Marc, et al. "A computational framework for the statistical analysis of cardiac diffusion tensors: application to a small database of canine hearts." IEEE transactions on medical imaging 26.11 (2007): 1500-1514.

Rapaka, Saikiran, et al. "LBM-EP: Lattice-Boltzmann method for fast cardiac electrophysiology simulation from 3D images." International Conference on Medical Image Computing and Computer-Assisted Intervention. Springer, Berlin, Heidelberg, 2012.

S. Rapaka, T. Mansi, B. Georgescu, A Kamen a nd D. Comaniciu. A System and Method for Fast Patient-Specific Cardiac Electrophysiology Simula tions for Therapy Planning and Guidance.

Relan, Jatin, et al. "Coupled personalization of cardiac electrophysiology models for prediction of ischaemic ventricular tachycardia." Interface focus 1.3 (2011): 396-407.

Rice, John Jeremy, et al. "Approximate model of cooperative activation and crossbridge cycling in cardiac muscle using ordinary differential equations." Biophysical journal 95.5 (2008): 2368-2390.

Roger, Véronique L., et al. "Heart disease and stroke statistics—2011 update: a report from the American Heart Association." Circulation 123.4 (2011): e18-e209.

Sermesant, Maxime, et al. "Patient-specific electromechanical models of the heart for the prediction of pacing acute effects in CRT: a preliminary clinical validation." Medical image analysis 16.1 (2012): 201-215.

Stergiopulos, Nikos, Berend E. Westerhof, and Nico Westerhof. "Total arterial inertance as the fourth element of the windkessel model." American Journal of Physiology—Heart and Circulatory Physiology 276.1 (1999): H81-H88.

Subramanian, Aravind, et al. "Gene set enrichment analysis: a knowledge-based approach for interpreting genome-wide expression profiles." Proceedings of the National Academy of Sciences 102.43 (2005): 15545-15550.

Ten Tusscher, K. H. W. J., and A. V. Panfilov. "Cell model for efficient simulation of wave propagation in human ventricular tissue under normal and pathological conditions." Physics in Medicine & Biology 51.23 (2006): 6141.

Toenjes, Martje, et al. "Prediction of cardiac transcription networks based on molecular data and complex clinical phenotypes." Molecular BioSystems 4.6 (2008): 589-598.

Trayanova, Natalia A. "Whole-heart modeling: applications to cardiac electrophysiology and electromechanics." Circulation research 108.1 (2011): 113-128.

Winslow, Raimond L., et al. "Integrative modeling of the cardiac ventricular myocyte." Wiley Interdisciplinary Reviews: Systems Biology and Medicine 3.4 (2011): 392-413.

Yang, Jason H., and Jeffrey J. Saucerman. "Computational models reduce complexity and accelerate insight into cardiac signaling networks." Circulation research 108.1 (2011): 85-97.

Zheng, Yefeng, et al. "Four-chamber heart modeling and automatic segmentation for 3-D cardiac CT volumes using marginal space learning and steerable features." IEEE transactions on medical imaging 27.11 (2008): 1668-1681.

SYSTEM AND METHODS FOR INTEGRATED AND PREDICTIVE ANALYSIS OF MOLECULAR, IMAGING, AND CLINICAL DATA FOR PATIENT-SPECIFIC MANAGEMENT OF DISEASES

CROSS-REFERENCE TO RELATED APPLICATIONS

This application claims priority to U.S. provisional application Ser. No. 61/668,201 filed Jul. 5, 2012, which is incorporated herein by reference in its entirety.

TECHNOLOGY FIELD

The present invention relates generally to methods and systems for integrated and predictive analysis of data items including, without limitation, molecular, imaging, and clinical data for patient-specific management of diseases.

BACKGROUND

Diseases such as cardiovascular disease (CVD) affect millions of patients in the United States. Proper clinical management of these diseases can be challenging and costly due to the various therapies and procedures required to provide effective disease treatment. For example, for heart failure (HF), proper clinical management of patients requires regular follow-up, expensive palliative therapies and, potentially, heart transplant. Additionally, for some diseases, treatments are not available. In these cases, clinical practice can only control the progression of the disease through medication or implantable devices. It is therefore crucial to identify the onset of the disease as early as possible to minimize its effect, and predict the progression of the disease in order to anticipate changes in lifestyle and treatments.

Early diagnosis and effective treatment planning and monitoring of a disease requires clinicians to gather data from various sources such as medical imaging, signal measurement, and molecular evaluation, to evaluate the disease as comprehensively as possible. While each of these techniques provides valuable information, each one of them, when taken individually, has its drawbacks. For example, molecular evaluation (e.g., based on blood samples or biopsies) may provide biomarkers of disrupted molecular pathways suggesting, for instance, the onset of a myocardial scar, fibrosis, or HF. However, the presence of abnormal biomarkers in laboratory tests does not provide any information regarding the location or dimension of the lesion. Conversely, imaging allows a clinician to quantify spatial and dynamic changes in heart morphology, structure and function. However, early stages of HF may not present visible symptoms like diminution of ejection fraction or presence of myocardium lesions, even if in vitro diagnostic (IVD) blood tests identified abnormal biomarkers.

Currently, clinicians perform and analyze imaging, signal, and molecular measurements independently, and then fuse the independent findings together at the end of the decision process, based on the clinician's experience or population-based guidelines. Data is not analyzed in a systematic and inter-dependent way. In some cases, data analysis is performed by different persons. This may result in sub-optimal diagnosis (with potentially contradictory conclusions), unnecessary monitoring, and not adapted therapies. Therefore, there is a need for a system that would integrate data items such as imaging, signal, and molecular data into a common framework for their joint analysis and interpretation.

SUMMARY

Embodiments of the present invention address and overcome one or more of the above shortcomings and drawbacks, by providing methods and systems for integrated analysis of molecular, imaging, and clinical data for patient-specific management of diseases. The methods and system described herein are especially applicable to the analysis of CVD and other cardiac diseases. However, one skilled in the art would recognize that the present invention may also be used to analyze non-cardiac diseases.

According to one aspect of the invention, a system operates in a plurality of modes to provide an integrated analysis of molecular data, imaging data, and clinical data associated with a patient. The system includes a multi-scale model, a molecular model, and a linking component operably coupled to the two models. The multi-scale model is configured to generate one or more estimated multi-scale parameters based on clinical data and imaging data associated with a patient when the system operates in a first mode. The multi-scale model is further configured to generate a model of organ functionality based on one or more inferred multi-scale parameters when the system operates in a second mode. The molecular model is configured to generate one or more molecular findings based on a molecular network analysis of the molecular data. When the system is in the first mode, the molecular model is constrained by the estimated multi-scale parameters. The molecular findings may identify, for example, one or more disrupted molecular pathways based on the molecular data. In some embodiments, the findings are also based on the estimated multi-scale parameters. The linking component is configured to transfer the estimated multi-scale parameters from the multi-scale model to the molecular model when the system operates in the first mode. The linking component is further configured to generate the inferred multi-scale parameters based on the molecular findings when the system operates in the second mode.

In some embodiments, the linking component generates the inferred multi-scale parameters using a cellular model parameter disruption module, a patient-specific cell model, and a cell model bridge. The cellular model parameter disruption module determines disrupted cellular model parameters based on the molecular findings. Then, the patient-specific cell model computes one or more cellular phenotypic characteristics based on the disrupted cellular model parameters. In one embodiment, the patient-specific cell model comprises an ion interaction model of cardiac electrophysiology configured to determine one or more indicators of the electrophysiological activity within a cell and an electromechanical coupling model configured to determine one or more indicators of patient-specific cell active force and one or more indicators of passive stress based on the indicators of electrophysiological activity within the cell. Finally, the cell model bridge generates the inferred multi-scale parameters based on the cellular phenotypic characteristics identified by the patient-specific cell model. In one embodiment, the system further includes a database of paired items, each paired item associating one or more known multi-scale parameters with one or more known cellular phenotypic characteristics. A machine learning process may be performed by the linking component by applying a machine learning algorithm to the database of paired items to compute the inferred multi-scale parameters based on the cellular phenotypic characteristics.

Embodiments of the present invention are also directed at computer-based methods for performing an integrated analysis of molecular data, imaging data, and clinical data from a patient. In this method, the linking component first receives molecular findings related to a disease from a molecular model. Then, it determines disrupted cellular model parameters based on the molecular findings. In some embodiments, the linking component determines the disrupted cellular model parameters based on the molecular findings by identifying one or more disrupted molecular pathways included in the molecular findings and modifying one or more cellular model parameters based on the disrupted molecular pathways. Next, the linking component computes one or more cellular phenotypic characteristics based on the disrupted cellular model parameters. In one embodiment, the linking component performs this computing by determining an indicator of electrophysiological activity within the patient; determining a patient-specific cell active stress indicator and patient-specific cell passive stress indicator; and computing the cellular phenotypic characteristics based on the indicator of electrophysiological activity within the patient, the patient-specific cell active stress indicator, and the patient-specific cell passive stress indicator. Finally, the linking component generates one or more disrupted multi-scale parameters based on the cellular phenotypic characteristics. In one embodiment, this generation includes three steps: creating a database of paired items, each paired item associating one or more known multi-scale parameters with one or more known cellular phenotypic characteristics; training a machine learning algorithm using the database of paired items; and applying a machine learning algorithm to the database of paired items to compute the disrupted multi-scale parameters based on the cellular phenotypic characteristics. The machine learning algorithm may be constrained based on the clinical data associated with the patient. Once, the disrupted multi-scale parameters are generated by the linking component, they may be used as input into a patient-specific multi-scale model to determine a phenotype prediction for the disease based on these parameters, thus achieving a link from molecular data to imaging.

In one embodiment, an ion interaction model of cardiac electrophysiology and a cellular model of electromechanical coupling model are used to identify the cellular phenotypic characteristics based on the disrupted cellular model parameters. More specifically, the ion interaction model of cardiac electrophysiology determines one or more indicators of the electrophysiological activity within a cell. Then, the electromechanical coupling model determines patient-specific indicators of cell active stress and indicators of passive stress based on the indicators of electrophysiological activity.

Various methods may be utilized to create the database of paired items. For example, in one embodiment, the database is created based on results previously calculated for other patients. More specifically, for each of a plurality of patients, a paired item is stored in the database of paired items, the paired item indicating an association between the multi-scale parameters and the cellular phenotypic characteristics associated with the respective patient. Alternatively, in some embodiments the database of paired items is created by utilizing a generalized (i.e., not patient-specific) multi-scale model to determine a plurality of first cellular phenotypes, each first cellular phenotype corresponding to distinct multi-scale parameters. A cellular model is utilized to determine a plurality of second cellular phenotypes, each second cellular phenotype corresponding to distinct cellular model parameters. For each first cellular phenotype that is equivalent to a second cellular phenotype, a paired item is stored in the database of paired items, the paired item indicating that an association between respective multi-scale parameters and respective cellular model parameters.

Embodiments of the present invention are also directed at computer-based method for performing an integrated analysis of molecular data, imaging data, and clinical data associated with a patient to determine an indication of disease severity and progression in the patient. A patient-specific multi-scale model determines one or more multi-scale parameters related to a patient phenotype based on the clinical data. Then a linking component generates an integrated phenotypic data set based on the multi-scale parameters. Next, a molecular model identifies one or more phenotype-specific subnetworks related to the patient phenotype based on the integrated phenotypic data set. Finally, an indication of disease severity and progression is determined based on the phenotype-specific subnetworks.

In some embodiments, the phenotype-specific subnetworks related to the patient phenotype are identified based on the integrated phenotypic data set by first establishing a set of subnetwork candidates, for example, by using the molecular model to identify subnetworks within the patient molecular network that include one or more genes related to cardiac functions. Then, the molecular model can be used to select one or more phenotype-specific subnetworks from the set of subnetwork candidates based on the integrated phenotypic data set. The set of subnetwork candidates may be established using any technique known in the art, but relying on the set of multi-scale parameters. In one embodiment, the phenotype-specific subnetworks are selected from the set of subnetwork candidates based on the integrated phenotypic data set according to a multi-step method. First, the molecular model identifies a plurality of related patients based on the integrated phenotypic data and determines related phenotypic data set corresponding to the related patients. Next, a t-test is applied between a first phenotype included in the integrated phenotypic data set and one or more second phenotypes included in the related phenotypic data set to generate t-test results. Then, the molecular model determines a level of dysregulation for each subnetwork candidate in the set of subnetwork candidates based at least in part on the t-test results. Lastly, the molecular model identifies the phenotype-specific subnetworks in the set of subnetwork candidates based on the level of dysregulation associated with each subnetwork candidate.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following figures.

DETAILED DESCRIPTION OF ILLUSTRATIVE EMBODIMENTS

The following disclosure describes the present invention according to several embodiments directed at the integrated analysis of data items including, without limitation, molecular, imaging, and clinical data for patient-specific management of diseases. The technology described herein is particular well suited to the analysis of cardiac diseases. However, one skilled in the art would recognize that the technology may be applied to analyze various diseases, including those that are not directly related to the heart.

Briefly, the present invention utilizes a model-based system comprising three components: a multi-scale model, which captures the biological phenomenon from cell to organ; a molecular model, which captures the molecular pathways from gene to cell; and a linking component, which connects the two models and therefore bridges molecular and clinical data together. The relationship of these components is as follows. First, the multi-scale model is used to 1) estimate the parameters of the multi-scale model from imaging data and clinical signals based on computational models of heart physiome, and 2) to predict phenotypic changes when these parameters are modified. Secondly, the molecular model is used to 1) identify, from multi-omics data, the molecular pathways that have been disrupted by the disease in the patient and 2) to provide disease-specific biomarkers. Finally, the linking component couples the two models together for integrated analysis. The system may offer two complementary modes, which can be executed independently or iteratively: a top-down mode, where clinical and imaging data further constrain the molecular analysis for more discriminative findings, and a bottom-up mode, which enables more discriminative analysis of imaging and clinical data but also the assessment of disease severity and prediction of therapy planning outcome. Thus, by integrating molecular data, imaging and other clinical information, the present invention may provide various benefits to physicians, including improving the early diagnosis of disease, enhancing disease monitoring, and informing therapy planning strategies.

Figure 1:
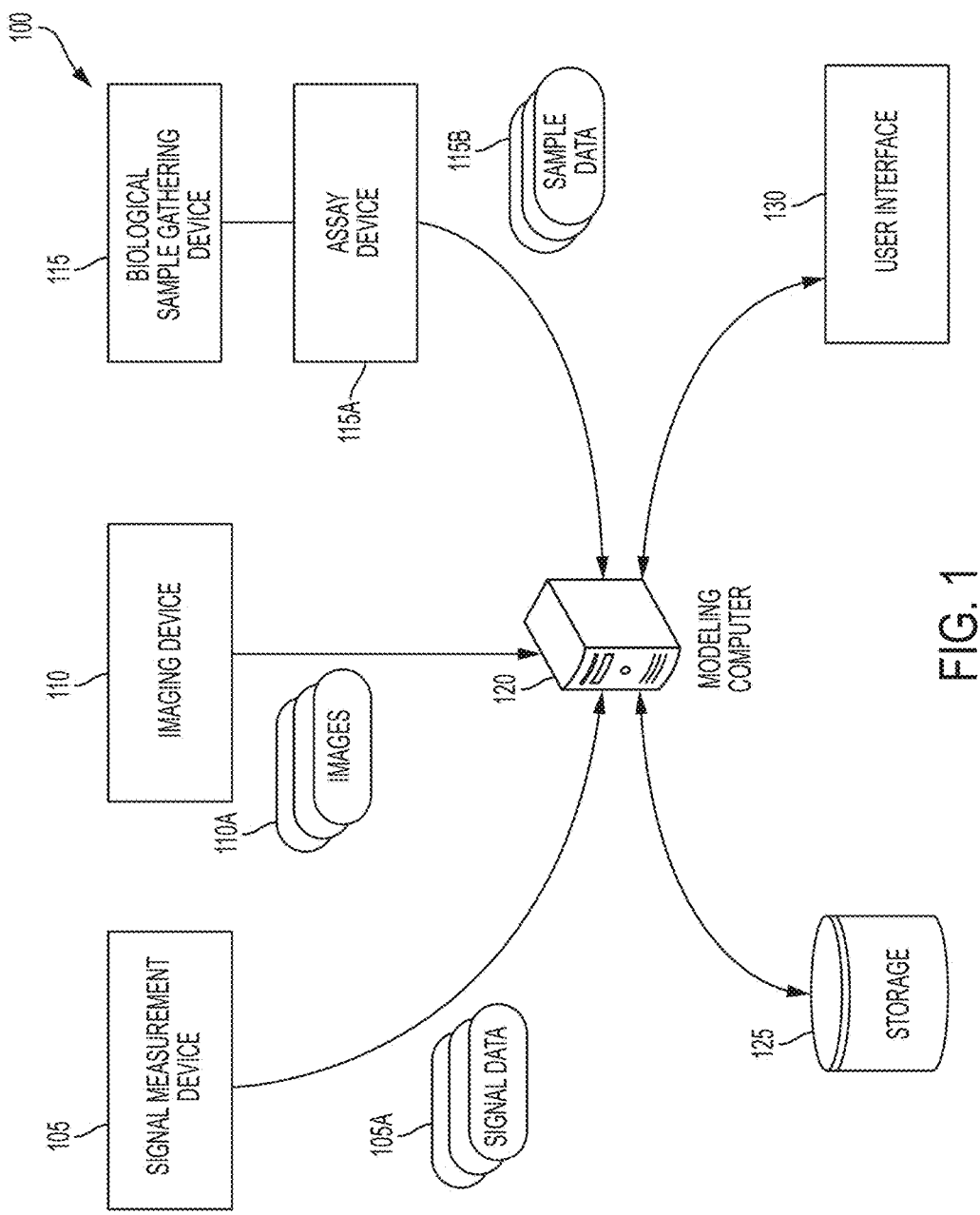
FIG. 1 is a system view of an integrated modeling system according to some embodiments of the present invention.

FIG. 1 is a system view of an integrated modeling system 100 according to some embodiments of the present invention. In the example of FIG. 1, three devices gather measurements about a biological system. First, a signal measurement device 105 captures measurements of physical quantities or impulses in the biological system referred to herein as signal data 105A. Examples of signal measurement devices include, without limitation, Electrocardiography (ECG) devices, Electroencephalography (EEG) devices, as well as devices which measure blood pressure, respiration, and/or oxygen saturation. Second, imaging device 110 captures images 110A of the biological system. Examples of imaging devices include, without limitation, Magnetic Resonance Imaging (MRI) devices, Computed Tomography (CT), ultrasound, angiography/fluoroscopy devices. Third, a biological sample gathering device 115 (e.g., blood sampling device) captures a biological sample and processes the sample via assay device 115A to produce sample data 115B. Examples of sample data 115B include, without limitation indications of histopathology, metabolites, protein profiles and concentrations, messenger and micro-RNA profiles, and sequence variants. It should be noted that the devices 105, 110, 115 illustrated in FIG. 1 are merely examples of the devices that may gather measurements of a biological system for transmission to the modeling computer. In other embodiments, different device configurations, some of which include additional devices, are used. Generally, any device which may provide measurements of a biological system may be used by the system 100 within the scope of the present invention.

Once gathered, the signal data 105A, images 110A, and sample data 115B are transmitted from the devices 105, 110, 115A, to a modeling computer 120. The modeling computer 120 includes one or more computational processing units (CPUs) and one or more graphical processing units (GPUs). As is well understood in the art, the use of CPUs in combination with GPUs provides various computation advantages in engineering applications, including a decreased latency in executing computationally intense algorithms. The measurement devices 105, 110, and 115A and the modeling computer 120 may be connected directly or indirectly using any technique known in the art. Thus, for example, in some embodiments the measurement devices 105, 110, and 115A and the modeling computer 120 are directly connected using a proprietary cable or an industry standard cable such as a Universal Serial Bus (USB) cable. In other embodiments, the measurement devices 105, 110, and 115A and the modeling computer 120 are indirectly connected over one or more networks (not shown in FIG. 1). These networks may be wired, wireless or a combination thereof. Additionally, in some embodiments, no physical connection exists between one or more of the measurement devices 105, 110, and 115A and the modeling computer 120. For these embodiments, a clinician may manually input data from the unconnected measurement device into the modeling computer 120.

Continuing with reference to FIG. 1, a user interface 130 is connected directly or indirectly to the modeling computer 120. The user interface 130 may include any interface known in the art including, for example and without limitation, a display, a keyboard, a mouse, and/or a touchscreen. Storage 125 is also connected, either directly or indirectly, to the modeling computer 125. In some embodiments, the modeling computer 120 may communicate with the storage 124 to retrieve measurement data (not shown in FIG. 1) as an alternative to receiving measurement data from measurement devices 105, 110, and 115A. Thus, for example, the modeling computer 120 can operate remotely from the measurement devices 105, 110, and 115A and/or use previously generated measurement data. Storage 135 may be implemented using any technique known in the art and may utilize, for example, any combination of magnetic, semiconductor, and optical storage media.

Figure 2:
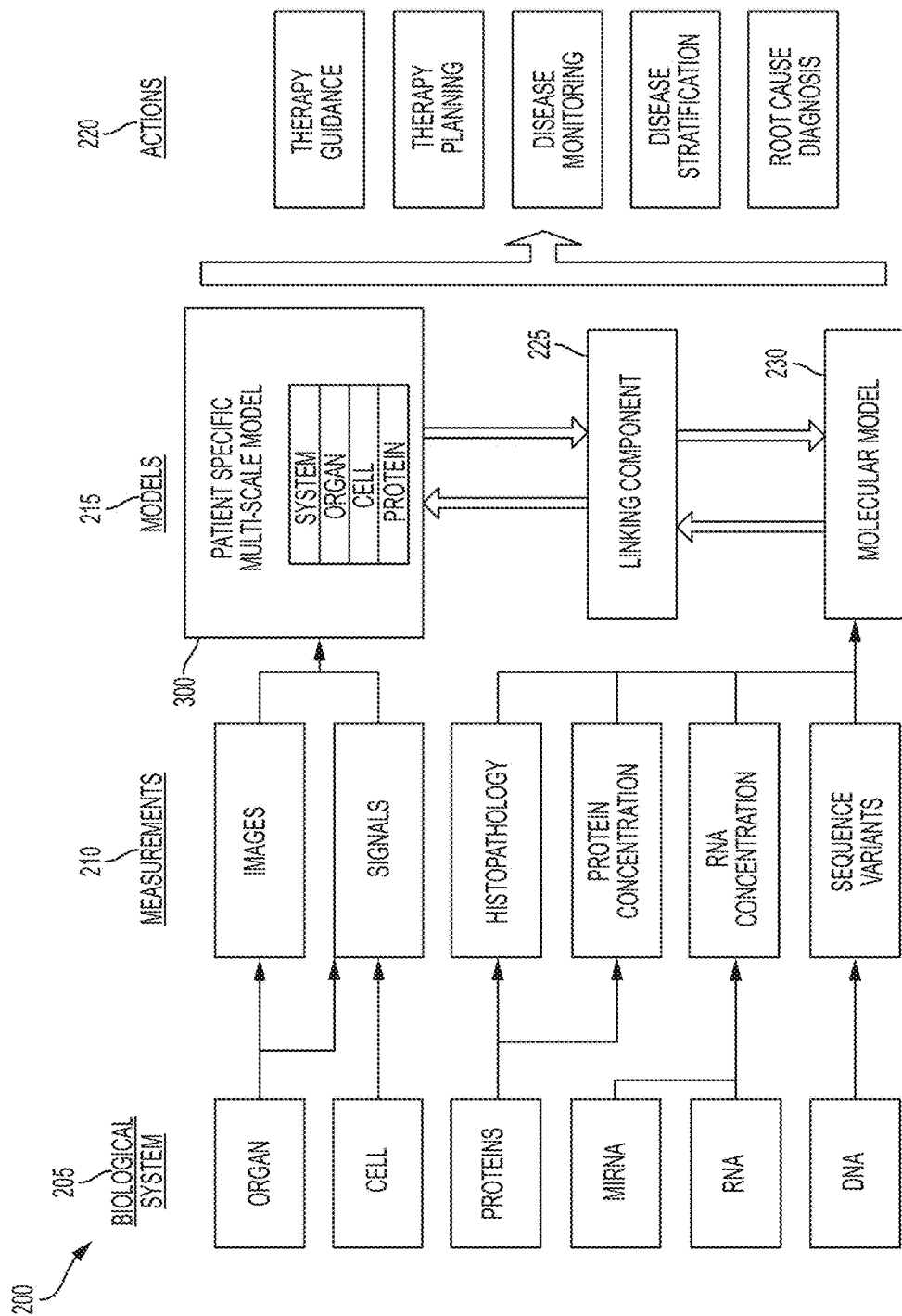
FIG. 2 provides a conceptual view of an integrated modeling system according to some embodiments of the present invention.

FIG. 2 provides a conceptual view 200 of the integrated modeling system 100 according to some embodiments of the present invention. Briefly, measurements 210 are acquired for various components of a biological system 205. These measurements 210 serve as input to models 215 which, in turn, provide information such that various actions 220s can be taken by a clinician. The example integrated modeling system 200 of FIG. 2 comprises three modules. First, a patient-specific multi-scale model 300 of heart function is computed for example, based on images and signals corresponding to organs and cells included in the biological system. Additionally in some embodiments, the multi-scale model 300 also estimates multi-scale model parameters that are not directly available from the image and signal data by fitting a multi-scale, phenomenological model of the heart function to the patient data using inverse problem algorithms. Examples of such multi-scale model parameters include, but are not limited to, tissue stiffness, electrical diffusion, and active contraction. The patient-specific multi-scale model 300 may be computed using any technique known in the art. Examples of techniques for computing the multi-scale model based on image and/or signal data are discussed generally in U.S. patent application Ser. No. 13/757,517 entitled "Method and System for Advanced Measurements Computation and Therapy Planning from Medical Data and Images Using a Multi-Physics Fluid-Solid Heart Model" and filed Feb. 1, 2013, the entirety of which is hereby incorporated by reference.

Continuing with reference to FIG. 2, a molecular model 230 analyzes various measurements made of data from the biological system 205 including, without limitation protein, miRNA, RNA, and DNA data. In the example of FIG. 2, these measurements include data resulting from the histopathological examination of proteins, measurements of protein concentration, measurements of miRNA and RNA concentrations, and identification of sequence variants based on DNA data. In other embodiments of the present invention, other measurements of protein, miRNA, RNA, and DNA data may be used.

In the example of FIG. 2, the linking component 225 integrates the patient-specific multi-scale heart model 300 and the molecular model 230 together. In some embodiments, the linking component 225 allows the two models 300, 230 to operate jointly according to two modes of operation. First, in a discriminative top-down mode, the patient-specific multi-scale heart model 300 may provide a parameter set to the linking component 225 which, in turn, can be used to generate molecular findings which are sent to the molecular model 230. This discriminative top-down mode may be used by clinicians, for example, for disease stratification and early diagnosis of disease. Second, in a generative bottom-up mode, the linking component 225 may use knowledge from the molecular model 230 to estimate multi-scale parameters which are then used to create or refine the patient-specific multi-scale heart model 300. The generative bottom-up mode may be used, for example, for disease progression prediction and therapy planning Additionally, since the bottom-up mode is generative, it can be utilized to predict and quantitatively monitor lesion aggressiveness (e.g. scar) and disease progression by inferring phenotypic changes given molecular measurements. Finally, in some embodiments, the two modes of operations can be combined in an iterative loop sequence, for more refined integrated analysis.

Figure 3:
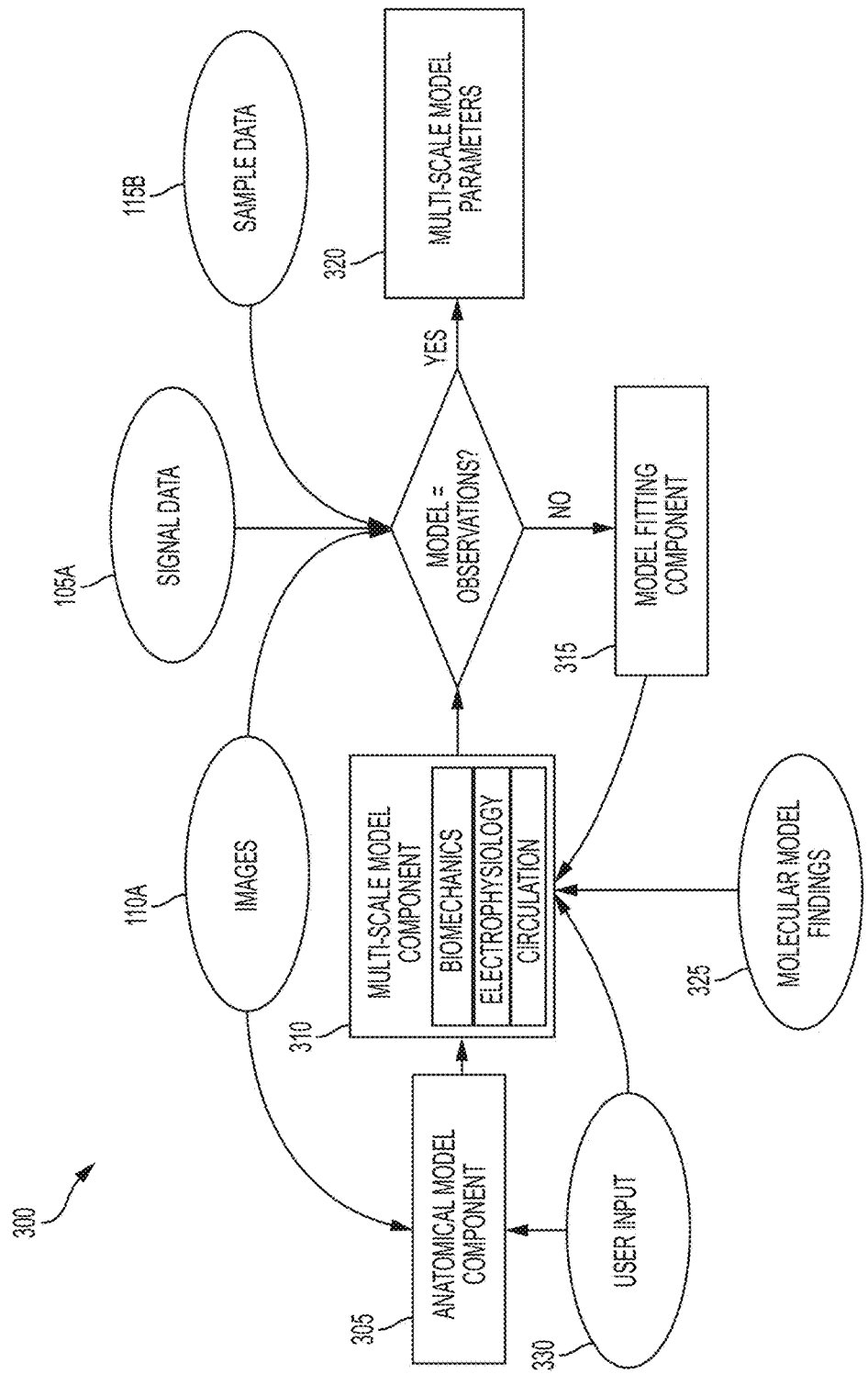
FIG. 3 illustrates a workflow of estimation of disrupted multi-scale parameters and a patient-specific multi-scale model based on an existing multi-scale model in some embodiments of the present invention.

FIG. 3 illustrates a workflow of estimation of disrupted multi-scale parameters and a patient-specific multi-scale model based on an existing multi-scale model in some embodiments of the present invention. As illustrated in FIG. 3, the multi-scale model 300 comprises three main components: an anatomical model component 305, a multi-scale model component 310, and a model fitting component 315. The anatomical model component 305 generates anatomical data based on images 110A (e.g., MRI, Ultrasound, and/or CT images) and user input 330 (e.g., therapy predictions). The generated anatomical data is used as input to the multi-scale model process 310 and may be further refined by additional input from the user. For example, key parameters may be modified to mimic therapies and predict their outcome. The anatomical model component 305 is described in greater detail below with respect to FIG. 4.

In some embodiments, molecular findings 325 obtained from the molecular model 230 are also used as input into the multi-scale model component 310. Inputting these findings allows the multi-scale model component 310 to predict organ phenotype based on molecular changes (gene, mRNA, miRNA, protein). As such, disease progression can be better quantified by predicting the changes in phenotype given the measured data.

Continuing with reference to FIG. 3, the output of the multi-scale model component 310, referred to herein as the "model data," is compared to observations made based on image data 110A, as well as additional data received by the model (e.g., signal data 105A and sample data 115B). If the model data does not match observations, a model fitting component 315 adjusts one or more parameters of the model and requests that model data be re-generated by the multi-scale model component 310. However, if the model data does match observations, the estimated parameters can be used as new, patient-specific multi-scale model parameters 320, which are not readily available in the data. These multi-scale model parameters 320 may include, for example, 3D maps of tissue stiffness, electrical diffusivity, maximum active contraction, z-disc stiffness, and/or actin-myosin cross-bridge strength. The workflow of the patient-specific multi-scale model component 310 is discussed in greater detail in U.S. patent application Ser. No. 13/757,517, entitled "Method and System for Advanced Measurements Computation and Therapy Planning from Medical Data and Images Using a Multi-Physics Fluid-Solid Heart Model" and filed Feb. 1, 2013, the entirety of which was incorporated by reference above. An illustration of the components of the multi-scale model component 310 is provided below with reference to FIG. 5.

Figure 4:
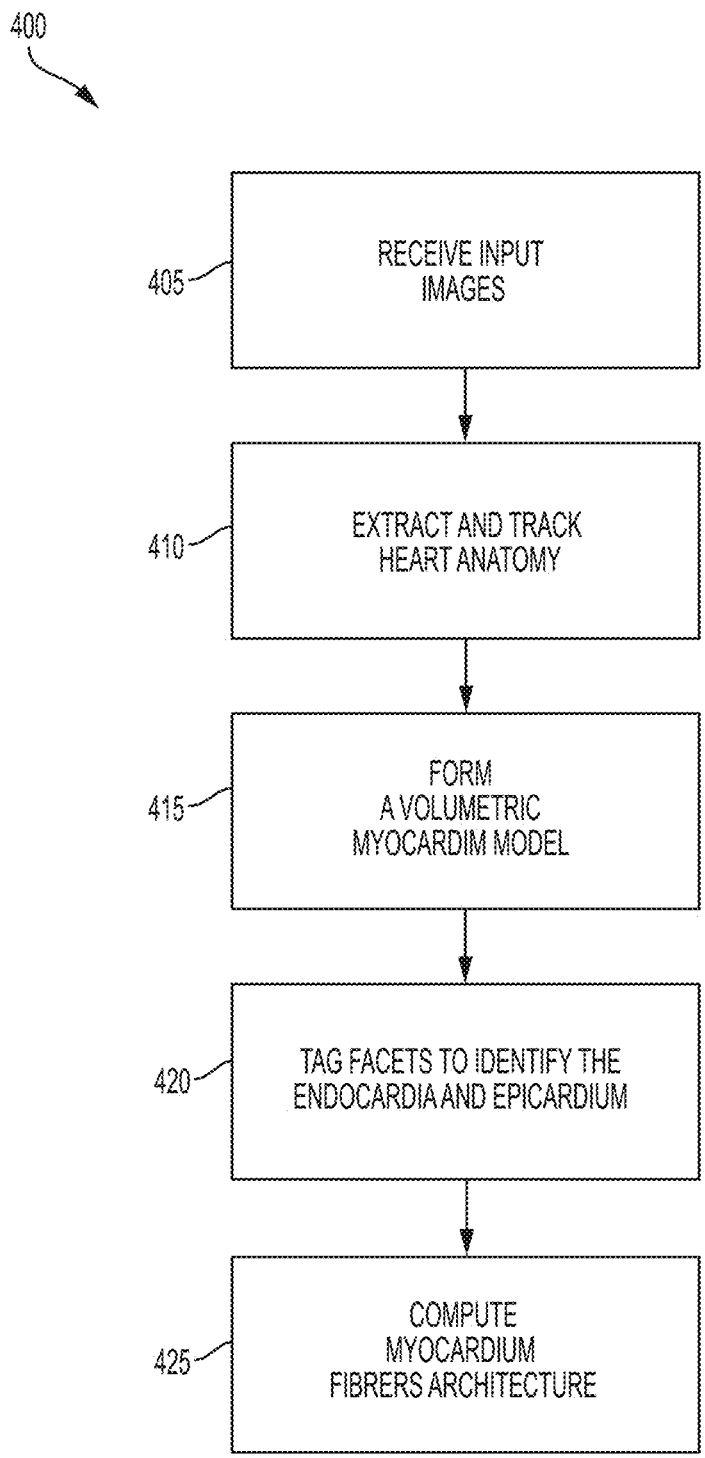
FIG. 4 illustrates an example of an anatomical model component according to some embodiments of the present invention.

FIG. 4 illustrates an example 400 of the anatomical model component 305 according to some embodiments of the present invention. At 405, input images 110A are received from one or more imaging devices 110. Next, at 410, one or more machine-learning algorithms (e.g., Marginal Space Learning algorithms) are applied to the input images 110A to extract and track the heart anatomy throughout the cardiac cycle. In one embodiment, step 410 results in a detailed 3D anatomical model of patient's beating heart, including a representation of the left ventricle, right ventricle, left atrium, right atrium, pulmonary artery outflow tract and aortic outflow tract. Valves may also be detected if visible in the input images 110A.

Continuing with reference to FIG. 4, at 415, the meshes representing the myocardium wall are fused and re-meshed to form a volumetric myocardium model. In one embodiment, the model is made up of tetrahedral elements. In other embodiments, other topologies (e.g. hexahedron) are used. Then, at 420, facets are tagged (automatically or manually by a clinician) to identify the endocardia and epicardium for model initialization and regional personalization. If scar images are available, myocardium scar extent and surrounding border zones may be automatically segmented and mapped to the volumetric model by tagging the elements that belong to these regions. The boundaries of these elements may be updated such that they conform to the underlying segmentation. Finally, at 425, the myocardium fibers architecture is computed. In one embodiment, a rule-based model of fiber architecture is employed according to ex-vivo observations. Future diffusion tensor MRI (DTI) or shear-wave imaging of fibers may also be mapped automatically to the anatomical model using standard image registration and tensor transport.

Figure 5:
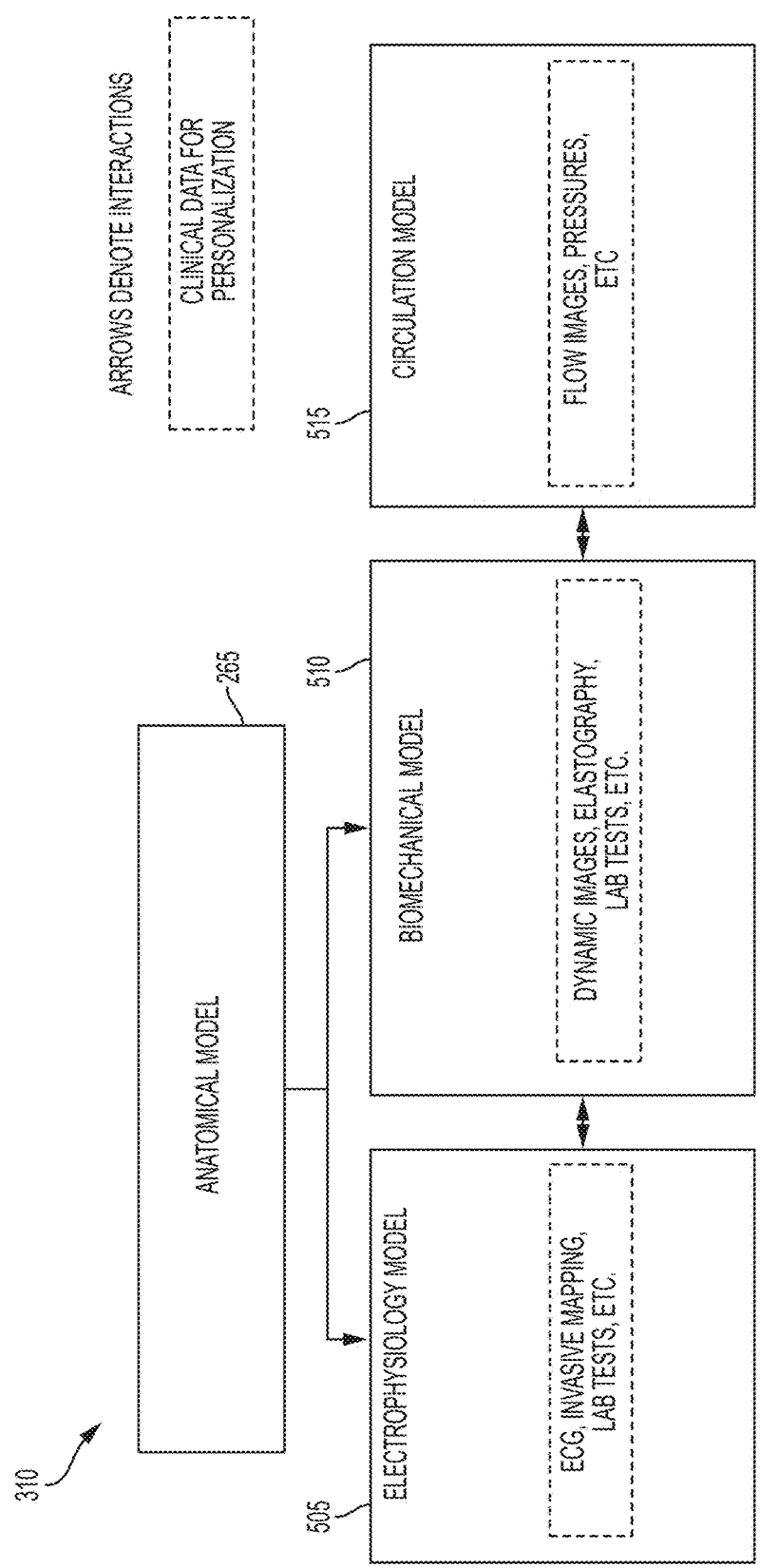
FIG. 5 provides an illustration of components of a multi-scale model component according to some embodiments of the present invention.

FIG. 5 provides an illustration of the components of the multi-scale model component 310 according to some embodiments of the present invention. The multi-scale model component 310 comprises three components: an electrophysiology model 505, a biomechanical model 510, and a circulation model 515. FIG. 5 provides one example of components that may be used in the multi-scale model component 310 and, in other embodiments, additional or alternative components may be used within the scope of the present invention. In the example of FIG. 5, the anatomical model 265 provides a model of patient anatomy and tissue structure corresponding to an organ of interest (e.g., geometry, scars, fibers, etc.) to the electrophysiology model 505 and a biomechanical model 510. The electrophysiology model 505 uses the anatomical data to simulate electric wave propagation across the organ. The information generated by the electrophysiology model 505 is used by the biomechanical model 510 to simulate cardiac contraction given passive and active properties of the organ's tissue (e.g., elasticity and/or viscosity). Finally, the circulation model 515 simulates blood flow throughout the organ. As noted in FIG. 5, each of the components of the multi-scale model component 310 can be personalized. For example, the biomechanical model 510 may be personalized with dynamic images of the organ, elastography, or laboratory test results.

The electrophysiology model 505 simulates electrical wave propagation in an organ of the biological system being modeled. More specifically, this model 505 computes the formation and propagation of action potential (i.e., the change in electrical potential associated with the passage of an impulse along the membrane of cells) in the organ. The characteristics of the electrophysiology model 505 may vary depending on the organ being modeled. For example, in one embodiment, the electrophysiology model 505 is a quasi-ionic, phenomenological model of cardiac electrophysiology for computing the formation and propagation of the action potential throughout the myocardium. With respect to computing the formation of action potential, in some embodiments, the electrophysiology model 505 captures clinical data associated with the organ (e.g., via ECG measurements, invasive mapping, or other laboratory testing procedures) and uses this data as input into a phenomenological cell model of action potential. The phenomenological cell model of action potential may utilize parameters that directly control the shape of the action potential and therefore can be estimated from the clinical data. Furthermore, the phenomenological cell model may include one or more variables that relate to lumped "in-flow" and "out-flow" currents, thus providing a functional link between the estimated parameters and a more detailed, ionic cell model of cardiac electrophysiology.

Once the formation of action potential is determined, the electrophysiology model 505 then computes its propagation throughout the organ. In one embodiment, the cell model is included into a reaction-diffusion equation that computes the propagation of the trans-membrane potential (mono-domain model). The reaction-diffusion equation may be controlled by two parameters: a tissue diffusion coefficient and an anisotropy coefficient. Numerical techniques, such as finite element methods, may be used to find approximate solutions to the reaction-diffusion equation. For example, in some embodiments techniques such as Lattice-Boltzmann Method for Fast Cardiac Electrophysiology Simulation ("LBM-EP") are used to compute the electrophysiology model 505 in real-time. The diffusion coefficient then can be estimated automatically, for example, from endocardial mapping and ECG. LBM-EP is described in greater detail in U.S. patent application Ser. No. 13/780,230, entitled "Method and System for Fast Patient-Specific Cardiac Electrophysiology Simulations for Therapy Planning and Guidance" and filed Feb. 28, 2013, the entirety of which is hereby incorporated by reference.

Figure 6:
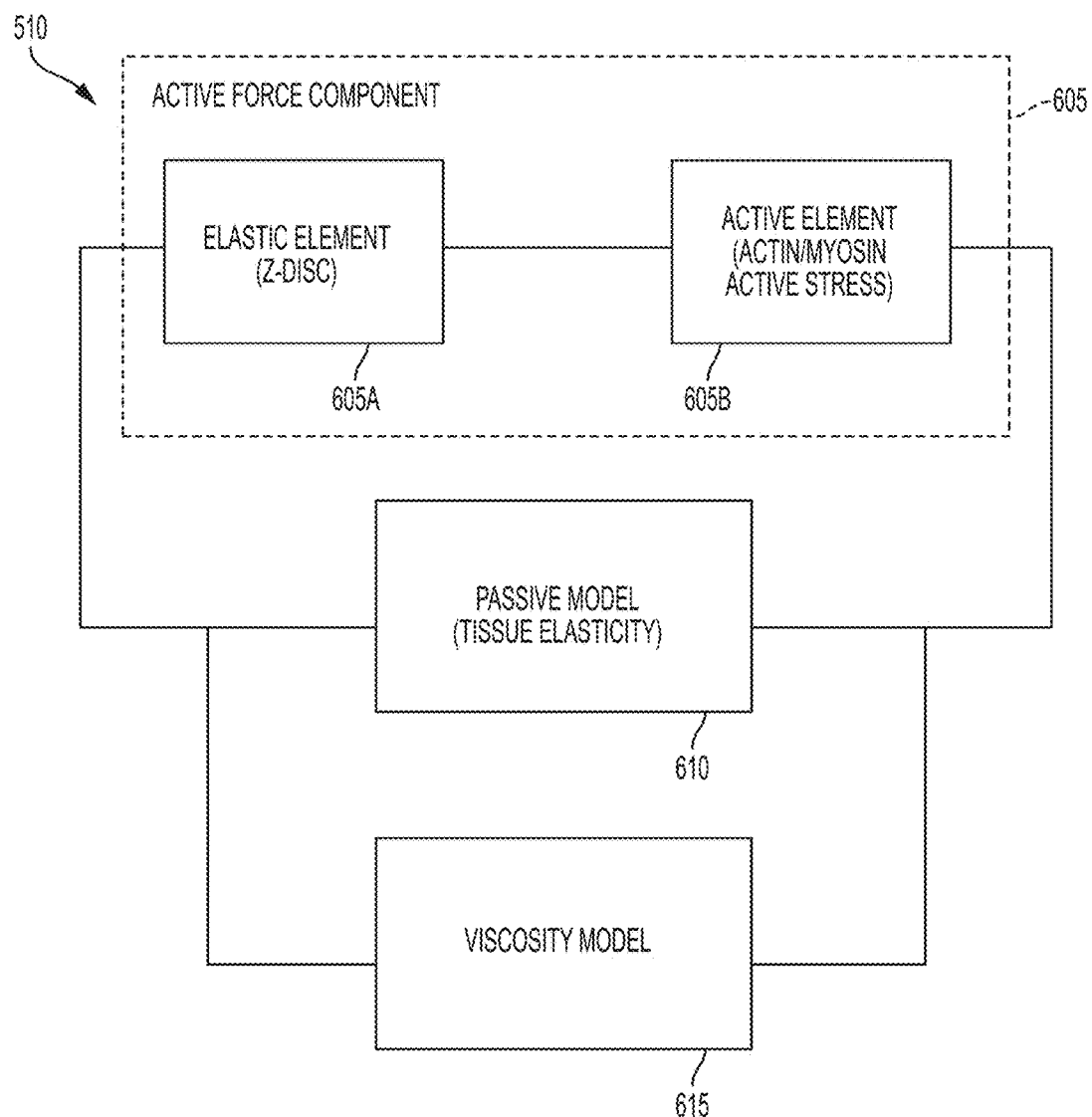
FIG. 6 illustrates components of a biomechanical model of a multi-scale model component, as configured in some embodiments of the present invention.

FIG. 6 illustrates the components of the biomechanical model 510 of the multi-scale model component 310, as configured in some embodiments of the present invention. The biomechanical model 510 integrates a multi-scale model of active cell force with a model of tissue elasticity and viscosity. In the example of FIG. 6, the biomechanical model 510 comprises an active force component 605, a passive model 610, and a viscosity model 615. The active force component 605 computes the active tensile stress generated by the interactions between cardiac myofibrils (e.g., actin, myosin, and/or troponin). An active element 605B in the active force component 605 computes the actin/myosin binding cycle under calcium concentration and ATP consumption. This translates into an anisotropic active stress along the fiber direction that is directly controlled by the electrophysiology model through calcium concentration. A second, elastic and passive element 605A in the active force component 605 is used to mimic the effects of the Z-discs. The elastic element 605A is used to capture isotonic contraction. The combination of the active element 605B and the elastic element 605A yields the active force model, which, is integrated over the anatomical model using, for example, finite element methods. One advantage of the selected model is that it may be controlled by seven parameters (z-disc stiffness, cross-bridge destruction rate, concentration factor of available cross-bridges, maximum strength, maximum active stiffness, ATP binding and release rates), which have a clear effect on the simulation and may be estimated from clinical images and data. At the same time, these parameters are related to molecular mechanisms. Thus, for example, the parameters may be related to detailed cellular models of myofibrils.

Continuing with reference to FIG. 6, the passive model 610 of the biomechanical model 510 may be used to compute the effects of tissue passive properties, mainly due to collagen matrix, on the global cardiac dynamics. The passive model 610 comprises an efficient anisotropic hyperelastic model. In one embodiment, when modeling cardiac behavior, the passive model 610 utilizes the orthotropic Costa law of myocardium biomechanics. In other embodiments, other laws may be used. Tissue incompressibility may be ensured using standard methods. The main parameter of the passive model 610 is tissue stiffness, which may be estimated automatically from the images. In some embodiments, a viscosity model 615 in the biomechanical model 510 is used to capture the viscous behavior of biological tissue. This component is optional and can be omitted, for example, if single-heart beat computations are performed in cardiac modeling. In one embodiment, the viscosity model 615 is a Rayleigh model of viscosity. In other embodiments, physiological models based on Prony series are used.

The circulation model 515 included in the patient-specific multi-scale model component 310 couples cardiac electromechanics with the hemodynamic boundary conditions. Thus, this circulation model 515 may be used to capture pressure overload, regurgitations, and other pathological features. In one embodiment, the ventricular pressure is modeled as a lumped variable (one for each ventricle). The pressure may be assumed to be spatially homogeneous inside a chamber and is computed based on the cardiac phase.

Figure 7:
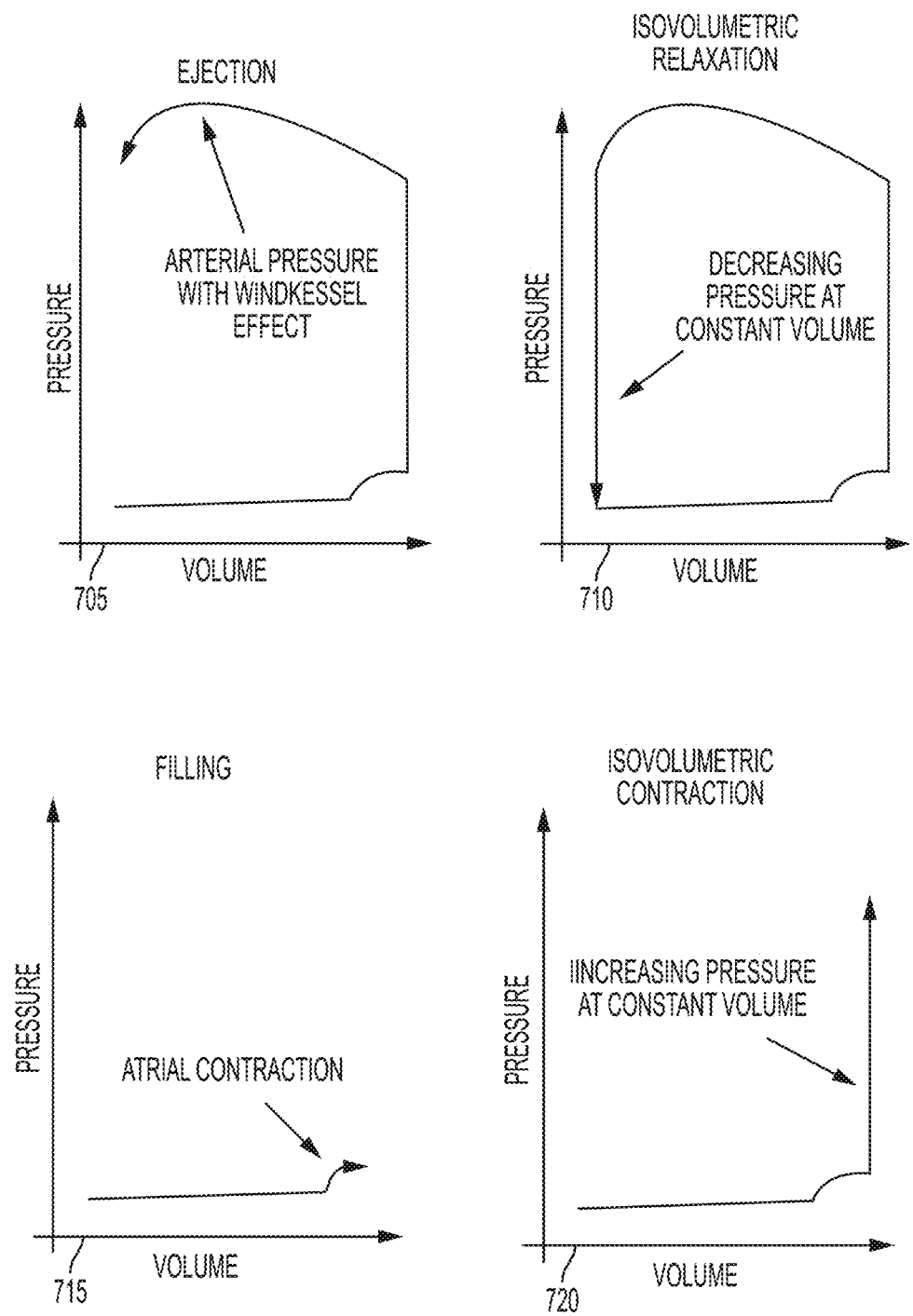
FIG. 7 illustrates phases and hemodynamic boundary conditions associated with a circulation model included in a patient-specific multi-scale model component.
Figure 8:
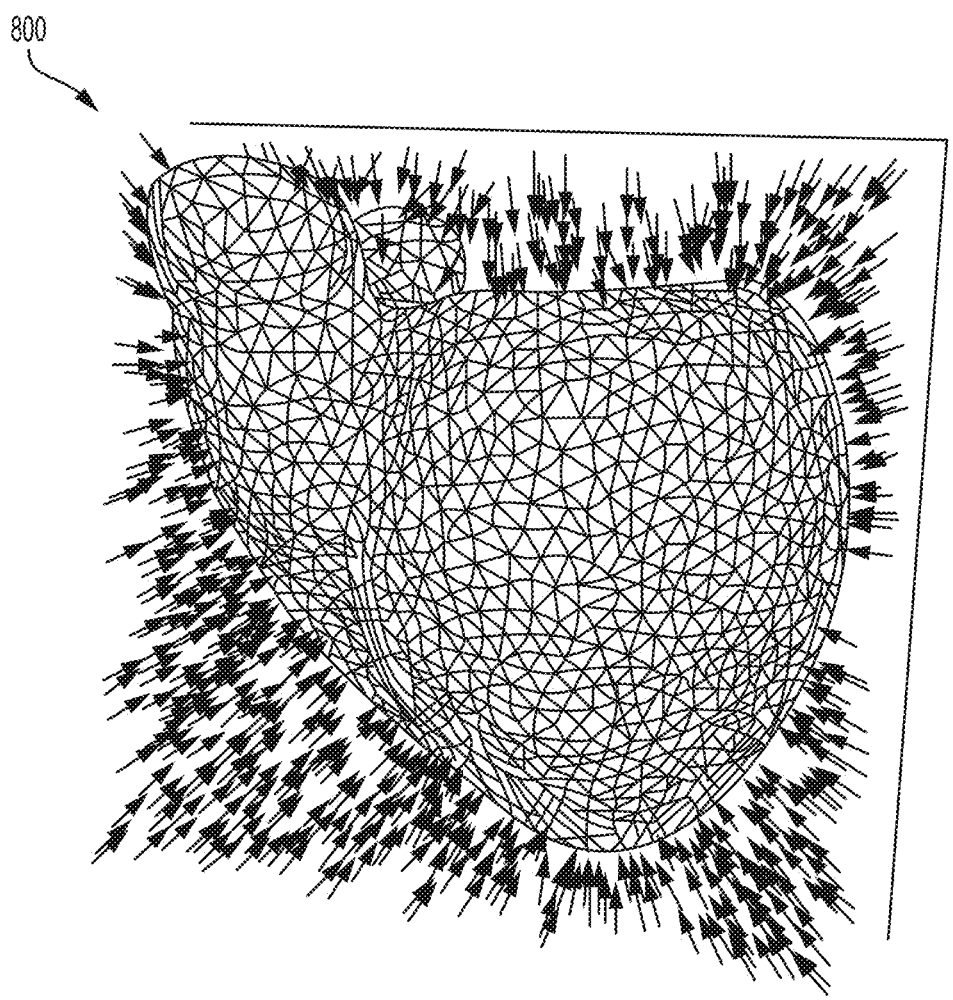
FIG. 8 illustrates a heart model at end-diastole with the pericardium force illustrated by arrows computed as a function of the gradient of the distance map from the pericardium used in one embodiment of present invention.

FIG. 7 illustrates the phases and hemodynamic boundary conditions associated with the circulation model 515 included in the patient-specific multi-scale model component 310. The circulation model is illustrated in four phases: ejection, iso-volumetric relaxation, filing, and iso-volumetric contraction. During the ejection phase 705, the ventricular pressure is equal to the arterial pressure. A lumped model of arterial compliance may be used to compute the arterial pressure based on the arterial flow. For example, in one embodiment a 3-element Windkessel model is used. When the heart starts to relax (change in ventricular volume variation), the arterial valves close and the ventricle enters in the iso-volumetric relaxation phase 710. The pressure may be calculated using a projection/prediction method while preserving ventricle volume. As soon as the ventricular pressure becomes lower than the atrial pressure, atrio-ventricular valves open and the ventricle proceeds to the blood filing phase 715. During the filing phase 715, the modeled ventricular pressure is equal to the atrial pressure. In one embodiment, a lumped model of active atrial contraction is used to compute the atrial pressure based on atrium compliance, volume, mitral flow and pulmonary vein pressure. When the heart starts to contract, the ventricle enters the iso-volumetric contraction phase 720. Atrio-ventricular valves close and the ventricular pressure starts to build up. Similar to the iso-volumetric relaxation phase 710, the iso-volumetric contraction phase 720 may utilize a projection/prediction method to compute the ventricular pressure while ensuring constant volume. In some embodiments, additional constraints are used to further refine the circulation model 515. For example, in one embodiment, a pericardium constraint is added to mimic the effects of the pericardium bag on the overall cardiac function. This constraint may be added, for example, by forcing the epicardial nodes of the model to stay inside an "allowed" region by applying a contact force as soon as they leave that region. The force may be computed automatically from the model at end-diastole as a function of the gradient of the distance map to the epicardium 800, as illustrated in FIG. 8. Additionally, springs may be attached at the valve plane to capture the stiffer boundary conditions of that region due to the tethered arteries and atria.

Figure 9:
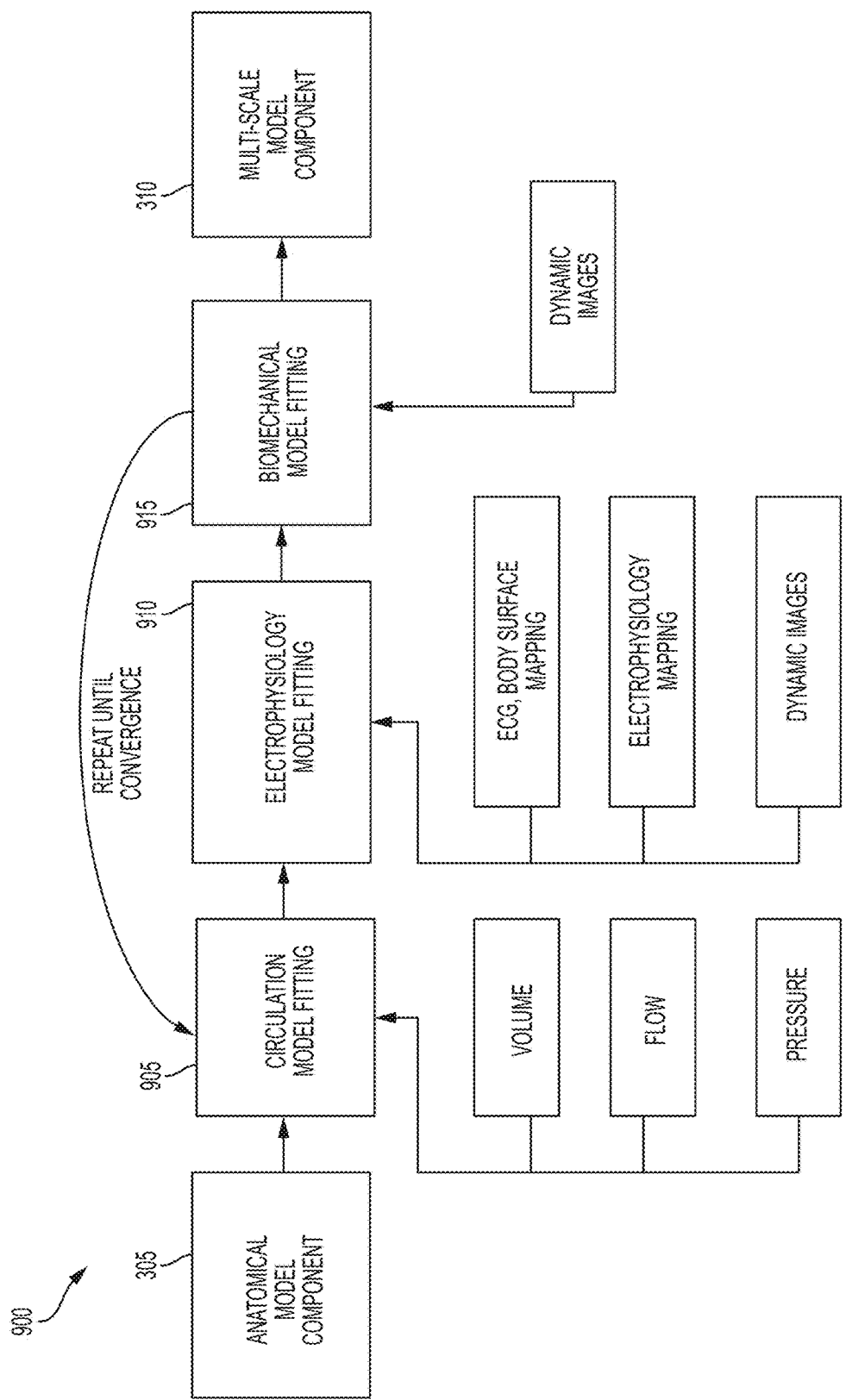
FIG. 9 illustrates an example of model fitting strategy that may be employed by a modeling fitting component, according to one embodiment of the present invention.

FIG. 9 illustrates an example of model fitting strategy 900 that may be employed by the modeling fitting component 315 illustrated in FIG. 3 for estimating the free parameters of the multi-scale mode component 310. The example of FIG. 9 shows how the strategy 900 may be employed for cardiac modeling. In a circulation model fitting component 905, the parameters of the circulation model 515 are first estimated from the cardiac chamber volumes, which are computed using the automatic heart tracking and patient-specific pressure/flow data (e.g., as determined by data from anatomical model component 305). Then, an electrophysiology model fitting component estimates the free parameters of the electrophysiology model 510 based on the available ECG, observed cardiac motion and endocardial/epicardial mapping (if available). Finally, a biomechanical model fitting component 915 estimates tissue stiffness and active stress such that the computed cardiac motion matches the myocardium dynamics observed in the images. The entire process iterates until convergence. At the end of this stage, the computational model of the heart is fitted to the patient's physiology. The set of free parameters that were estimated represent multi-scale model parameters that may be utilized, for example, by a cardiologist for diagnosis and patient management. In some embodiments, to optimize the computation time and robustness associated with the, a marginal approach may be employed. Additional details of the model fitting strategy are described in U.S. patent application Ser. No. 13/757,517, entitled "Method and System for Advanced Measurements Computation and Therapy Planning from Medical Data and Images Using a Multi-Physics Fluid-Solid Heart Model" and filed Feb. 1, 2013, which was incorporated by reference above.

Figure 10:
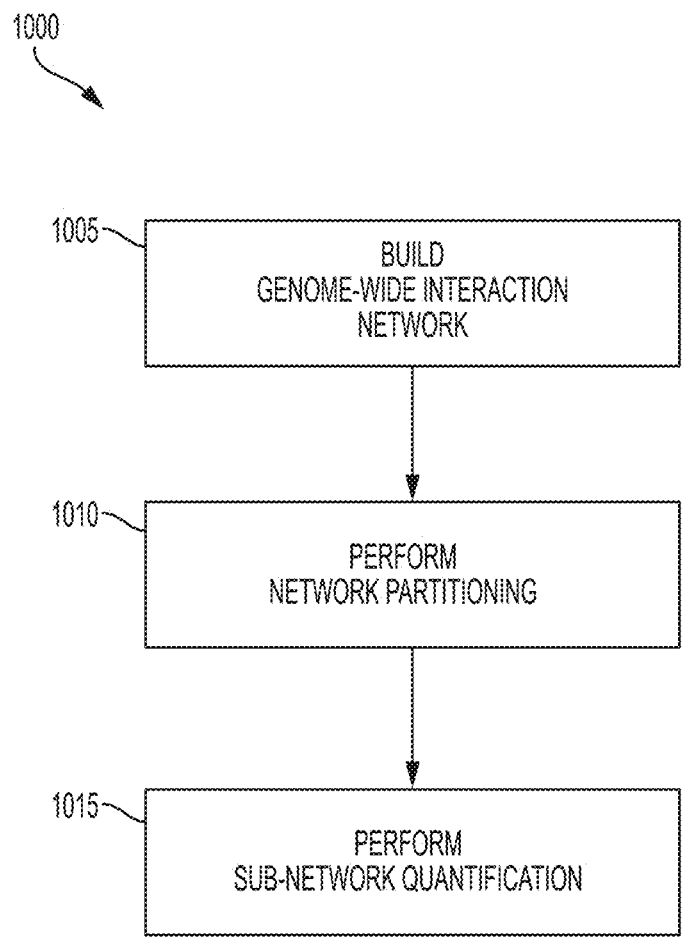
FIG. 10 illustrates a process used by a molecular model for building a representation of a molecular interaction network, according to some embodiments of the present invention.

FIG. 10 illustrates a process 1000 used by the molecular model 230 for building a representation of a molecular interaction network according to some embodiments of the present invention. As is well understood in the art, a molecular interaction network represents the backbone of activities in a cell, and every cell has its unique molecule-molecule wiring diagram. Thus, molecular interaction networks provide information regarding the dynamics of molecular networks underlying cellular processes related to human disease. At 1005, a genome-wide interaction network is reconstructed based on, for example, knowledge-driven algorithms and/or data-driven algorithms. In embodiments where knowledge-driven algorithms are used, the network is reconstructed based on information extracted from databases of biological interactions and functional annotations.

These databases may be created, for example, from individually modeled relationships between genes, transcripts, proteins, complexes, cells, tissues, metabolites, drugs, and diseases. In embodiments where data-driven algorithms are used to reconstruct the molecular interaction network, high-throughput omics data may be generated, for example, from cell perturbations or sampled across various phenotypes. Next, candidates for inclusion in the molecular interaction network are identified from the omics data. Once these candidates have been identified, various methods can be used to measure the dependence between two candidates and determine the structure of the network. These methods may include, for example, correlation-based or mutual information-based algorithms. Additionally, both correlation and partial correlation (or mutual information and data processing inequality) may be used on gene expression data to infer the direct influence between two candidates, with the effect of other candidates being removed.

At 1010, the genome-wide interaction network is partitioned into smaller sub-networks. This partitioning may be performed using, for example, one or more graph clustering or community detection algorithms known in the art. In some embodiments, the network is analyzed to identify clusters of nodes such that the nodes inside a cluster are tightly connected and the nodes in different clusters are weakly connected. In one embodiment, a isoperimetric graph clustering algorithm is used to approximate the solution to this problem by randomly selecting a reference point and then ranking all other nodes by how tightly connected they are to the reference node. The rank for "tightly connected" nodes is derived by the expected number of steps a random walker would have to take from each node to reach the reference node. Since random walks effectively explore parallel paths in the network, this measure ranks nodes as "tightly connected" when they have many parallel paths to reach the reference node and less tightly connected when there are few parallel paths to reach the reference node. Therefore, nodes with a high rank have many parallel paths to the reference node (i.e., belong to a tightly connected set of nodes in the same cluster as the reference) and nodes with a low rank have few parallel paths connecting them to the reference node (i.e., belong to a different cluster which is weakly connected). In this way, a threshold of the ranking may be chosen to optimize the within-cluster connectivity of the two partitions and minimize the between-cluster connectivity.

Continuing with reference to FIG. 10, at 1015, once the subnetworks have been identified, they may be quantified for the level of dysregulation in each patient based on whole-genome sequencing data and/or gene expression data. For whole-genome sequencing data, a subnetwork dysregulation can be defined as the normalized count of genetic variants for genes in each subnetwork (i.e., the ratio of the number of variants to the number of genes and gene length) and the predicted variants' functional effect (e.g. non-synonymous mutation) such that higher normalized count and disruptive variant effects will constitute to a higher level of dysregulation. For the gene expression data, a z-score may be calculated for each gene based on its respective gene expression. Then, in each sample, genes may be sorted by their z-score and used as the reference list in Gene Set Enrichment Analysis (GSEA). The subnetwork expression may be approximated by the Normalized Enrichment Score (NES) computed for all nodes in the subnetwork. The standard GSEA may be applied directly to PPI network, but for the transcriptional network, where each subnetwork includes both activated and repressed genes, GSEA2 may be used instead. As is well understood in the art, GSEA2 is an extended version of GSEA that assess enrichment of two complementary gene sets (e.g. pro-apoptotic & anti-apoptotic gene sets) at once. A new subnetwork expression matrix (e.g., NES values) can then be generated, where each row represents a subnetwork (instead of gene) and each column represents a patient sample.

Figure 11:
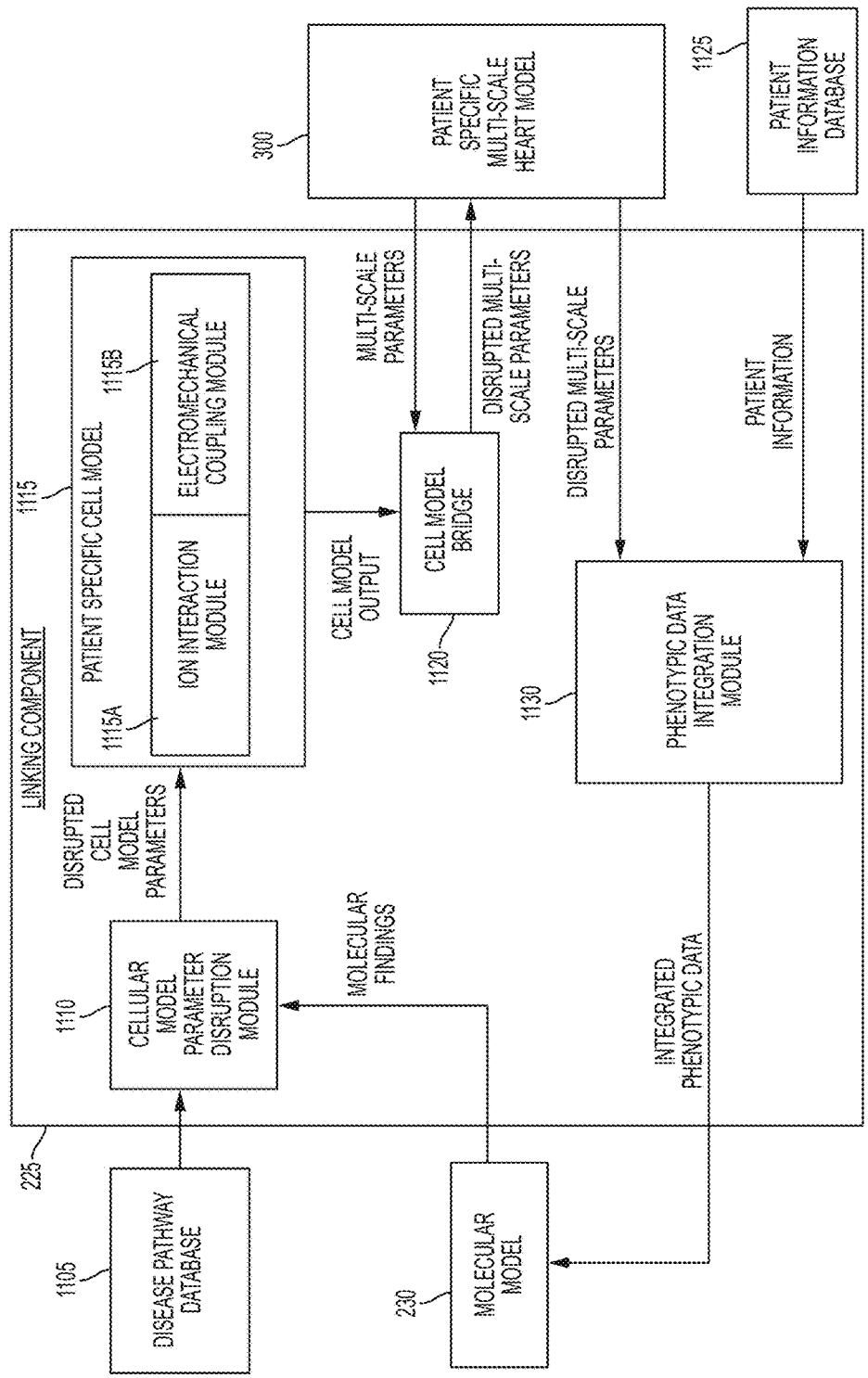
FIG. 11 provides an illustration of a linking component according to some embodiments of the present invention.

FIG. 11 provides an illustration of the linking component 225 according to some embodiments of the present invention. The linking component 225 provides two link modes to bridge the molecular model 230 and the multi-scale model 300, used independently or simultaneously according to the targeted application (e.g., disease stratification and/or disease progression prediction). The two approaches depend on whether the multi-scale heart model 300 or the molecular model 230 is used for the starting point of the analysis. In the first mode, referred to herein as the "top-down" mode, the patient specific multi-scale heart model 300 is used to generate input, via the linking component 225, for the molecular model 230. Conversely, in the second mode, referred to herein as the "bottom-up" mode, the molecular model is used to generate, through the linking component 225, the multi-scale parameters that are used in the multi-scale model 300 to predict the phenotype due to the changed molecular pathways. The elements of the linking component are described in greater detail below with respect to FIGS. 12-15.

Figure 12:
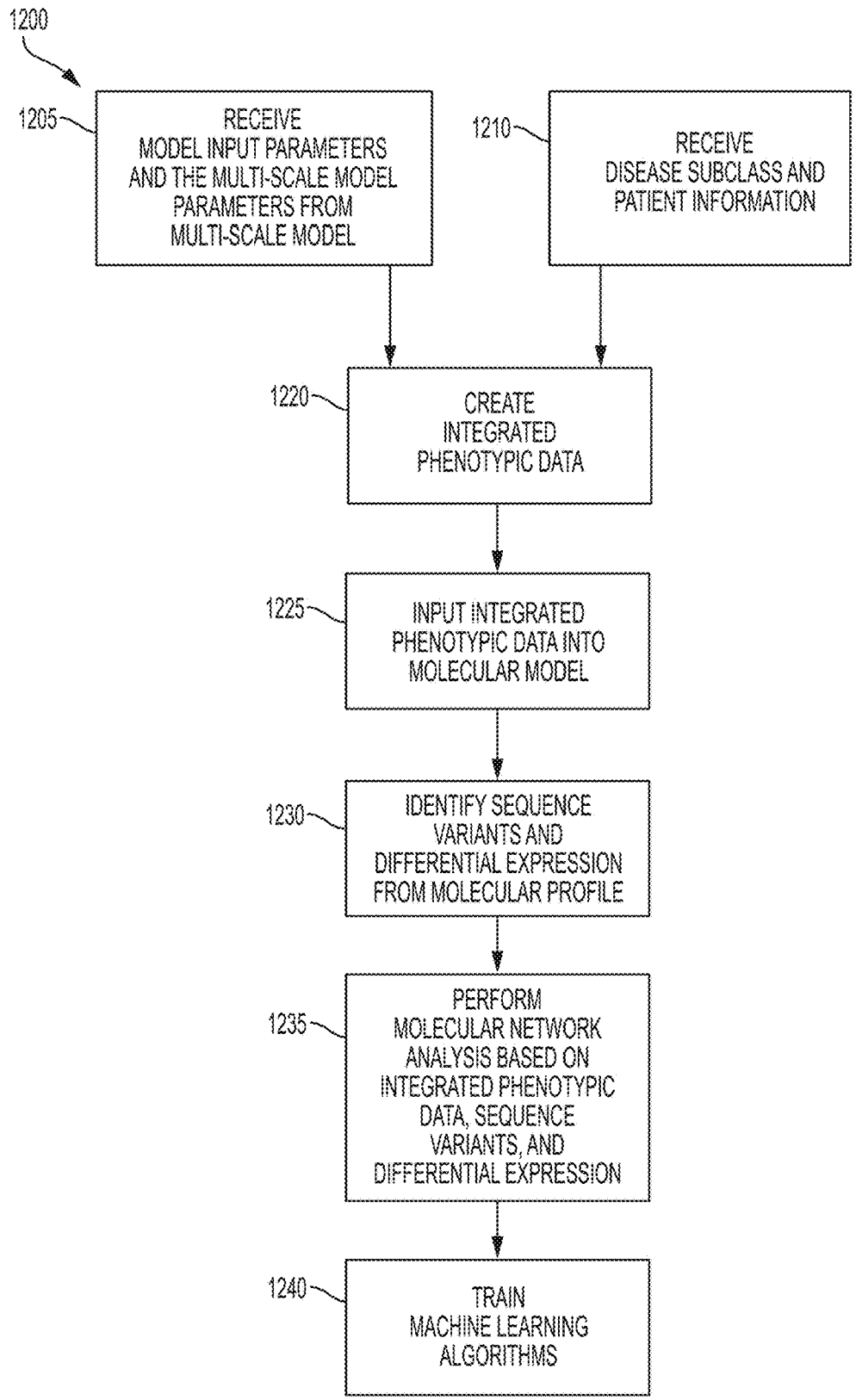
FIG. 12 provides an illustration of a process performed by a linking component in a top-down mode, according to one embodiment of the present invention.

FIG. 12 provides an illustration of the process 1200 performed in top-down mode in some embodiments of the present invention. The example of FIG. 12 illustrates how the top-down mode can be used for molecular network analysis constrained by clinical data such as image data and signal data. However, it should be understood, that the top-down mode may be applied to other types of analysis as well. Briefly, the top-down mode creates integrated, detailed phenotypic data based, in part, on the multi-scale model parameters 320 generated by the multi-scale model 300. This phenotypic data aids in the identification of disrupted molecular pathways, relevant biomarkers, and regulatory mechanisms causing the disease-related phenotype. Example applications of the top-down mode include, without limitation, early diagnosis of heart failure and risk stratification (e.g., identification of severity of the disease, aggressiveness of the lesions, etc.).

In the process 1200 illustrated in FIG. 12, at 1205, model input parameters and the multi-scale model parameters from the multi-scale model 300 are received by the phenotypic data integration module 1130 in the linking component 225. The model input parameters may include, for example, parameters associated with generating the system-level, organ-level, cellular-level, and/or protein-level model data. As noted previously, the multi-scale model parameters 320 generated by the multi-scale model 300 may include, for example, 3D maps of tissue stiffness, electrical connectivity, maximum active contraction, z-disc stiffness, and/or actin-myosin cross-bridge strength. At 1210, the phenotypic data integration module 1130 receives disease subclass information and/or patient information from a patient information database 1125. The subclass information and/or patient information may be received, for example, via input by a clinician or via retrieval from a database of information based on one or more variables (e.g., patient characteristics) specified by the clinician. In one embodiment, the subclass information corresponds to standardized classification system such as the New York Heart Association Functional Classification. The patient information may comprise any information that the clinician believes to be useful in focusing the molecular analysis of the patient. For example, in one embodiment, the patient information comprises medical information corresponding to one or more family members of the patient (i.e., a "family history"). At 1220, the phenotypic data integration module 1130 combines the received model input parameters, multi-scale model parameters, disease subclass information, and/or patient information into a data set referred to herein as integrated phenotypic data.

Continuing with reference to FIG. 12, steps 1230 to 1235 are performed by molecular model 230. At 1230, omics data analysis is performed on molecular profile information (e.g., sequence information and/or expression information) to determine sequence variants and differential expression data. Then, at 1235, molecular network analysis is performed based on the integrated phenotypic data, the sequence variant data, and the different expression data. This analysis results in the identification of one or more patient-specific molecular subnetworks. This molecular analysis is described in detail below, with reference to FIG. 13. Finally, at 1235, the identified molecular sub-network is used to train one or more machine learning algorithms in order to make predictions about the disease. For example, in one embodiment, this training results in predictions about a disease progression. In other embodiments, other characteristics of the disease are predicted.

Figure 13:
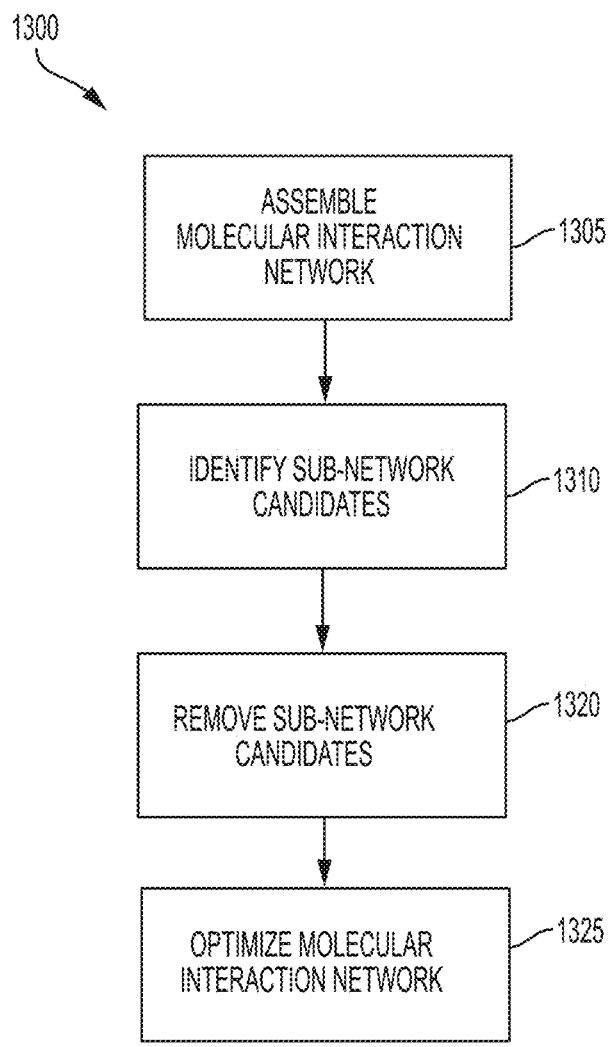
FIG. 13 provides an overview of the process used by a molecular model to perform molecular network analysis included in a linking component when operating in a top-down mode, according to one embodiment of the present invention.

FIG. 13 provides an overview of the process 1300 used by a molecular model 230 to perform molecular network analysis included in a linking component 225 when operating in a top-down mode, according to one embodiment of the present invention. At 1305, a molecular interaction network is assembled by applying one or more reverse engineering algorithms to measurement data 210 received by the molecular model 230. Once the molecular interaction network has been assembled, at 1310, one or more candidate sub-networks are identified in the molecular interaction network. For example, in some embodiments, sub-networks containing genes known to involve in cardiac-related functions may be identified at 1310 as candidate sub-networks. Additionally, in some embodiments, the integrated phenotypic data (see 1220 in FIG. 12) is used to identify one or more homogeneous groups of patients and select sub-network candidates based on association studies with the groups. For example, the organ level input parameters may be categorized to generate finer granularity of phenotypes, and a T-test between any two extreme phenotypes can be applied to the quantified sub-network expression to identify the phenotype-specific sub-networks. The continuous value of the input parameters may also be used in this case by applying the correlation-based approaches to discover the relevant candidate sub-networks.

Once the sub-network candidates have been identified, one or more candidates may be removed at 1320 based on exclusion criteria supplied by the user or, alternatively, designed into the molecular model 230. For example, in one embodiment, sub-networks that are not significant in both T-test and correlation studies are removed from the candidates originally identified at 1310. Then, at 1325, the size of the selected sub-networks may be optimized. For example, in some embodiments, adjacent sub-networks are merged if both sub-networks are associated with a specific phenotype. In other embodiments, other criteria are used for merging sub-networks.

Figure 14:
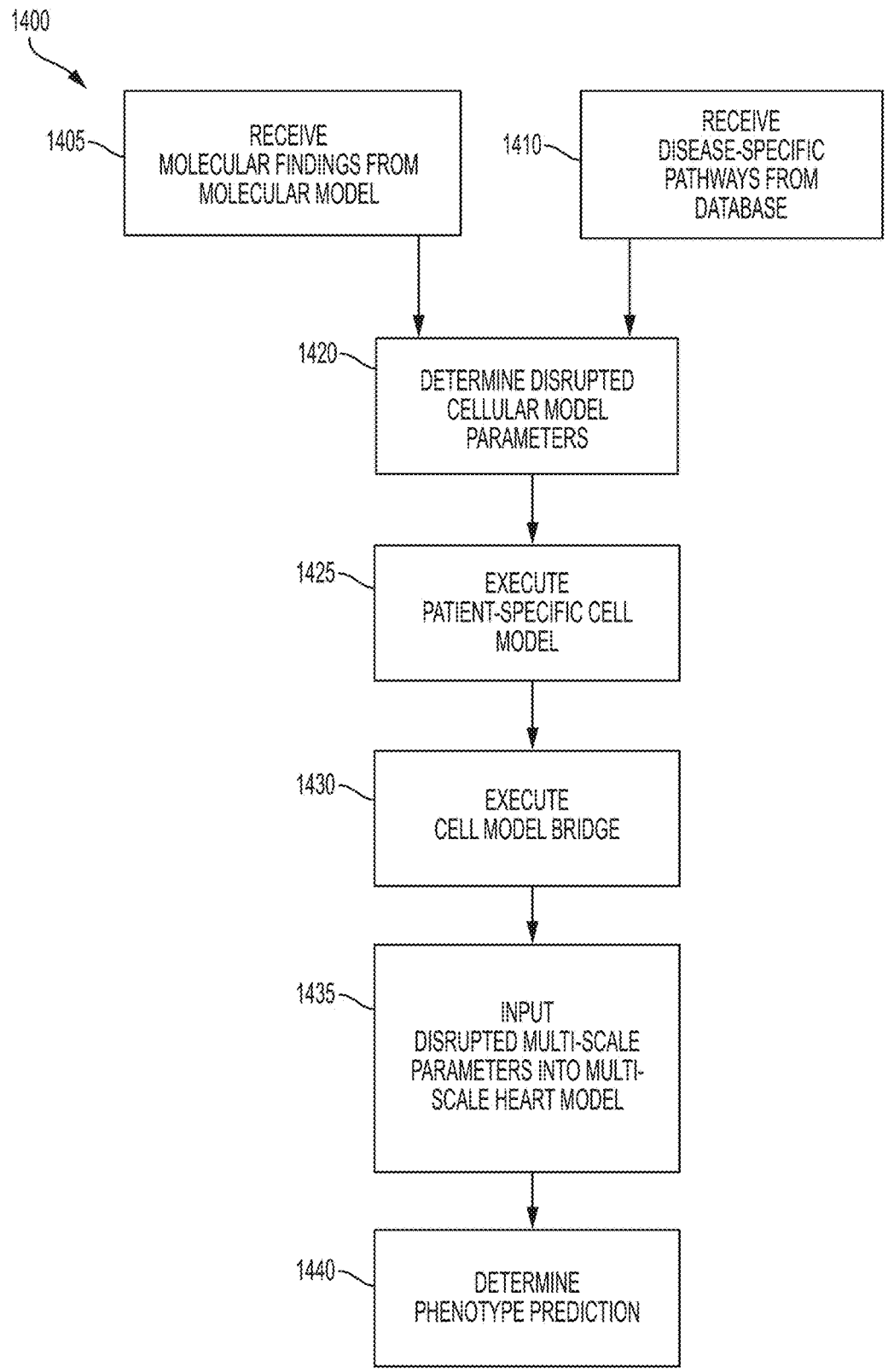
FIG. 14 provides an illustration of a process performed by a linking component when operating in a bottom-up mode according to one embodiment of the present invention.

FIG. 14 provides an illustration of a process 1400 performed by the system 200 when operating in bottom-up mode in some embodiments of the present invention. In this mode, the findings returned by the molecular model 230 are utilized as input to the multi-scale model 310 to predict information such as cardiac phenotype, severity of visible lesions, therapy outcomes. The molecular model 230 and the multi-scale model 330 are linked through two main elements of the linking component 225: a patient-specific cell model 115 and a cell model bridge 1120.

The example process 1400 of FIG. 14 begins by determining parameters for the patient-specific cell model 115. The patient-specific cell model 115 includes a set of standardized parameters established based on previously generated experimental results available, for example, in literature, commercial databases, or academic database known in the art. These standardized parameters are modified based on the molecular pathways and biological processes of the patient. Returning to FIG. 14, at 1405, a disruption module 1110 in the linking component 225, receives molecular findings from the molecular model 230. At 1410, the disruption module 1110 receives disease-specific pathway data, for example, from an external database 1105 of experimental results previously generated. Then, at 1420, the disruption module 1110 uses the disease-specific pathway data to map the molecular findings into parameters for the patient-specific cell model 1115. More specifically, the disruption module 1110 identifies the molecular pathways and/or biological processes that are disrupted in the patient and, based on this identification, modifies parameters for the patient-specific cell model 115 accordingly. The modified parameters are referred to herein as disrupted cellular model parameters.

Continuing with reference to FIG. 14, at 1425, the disrupted cellular model parameters are used as input into a patient-specific cell model 1115. The patient-specific cell model comprises one or more cell scale models known in the art. For example, in some embodiments, the patient-specific cell model 1115 comprises an ion interaction model 1115A and an electromechanical coupling model 1115B. The ion interaction model 1115A computes the state of every known ion channel and the current that goes through these channels during a cell contraction cycle. The electromechanical coupling model 1115B couples the electrophysiological activity (computed using the ion interaction model) with sliding myofilaments (e.g., actin/myosin) to compute the stress generated by the cell according to its current molecular state. In some embodiments, the electromechanical coupling model 1115B captures the mechanisms involving the sarcoplasmic reticulum, calcium-induced-calcium-release pathway, and/or the actin/myosin pathway. In these embodiments, the electromechanical coupling model 1115B may also capture dynamics-dependent behaviors, such as the variation of the generated stress with respect to the length of the cell. As a result, any identified misregulation in these pathways by the molecular model can be mapped to compute a patient-specific cell active stress. The ion interaction model 1115A and electromechanical coupling model 1115B may be coupled together, for example, through the calcium concentration variable [Ca2+], which controls the calcium-induced-calcium release cycles and therefore the timing and strength of the active stress. The outputs of the patient-specific cell model 1115 may include various values associated with the kinetic and electrophysiological effects of molecular changes on cell function. For example, in one embodiment, these values include the shape and timing of the action potential, strength of the cell stress, and other phenotypic information at the cellular level. At 1430, these values are used to execute the cell model bridge 1120 in order to calculated disrupted multi-scale parameters. The execution of the cell model bridge 1120 is described in greater detail below with respect to FIG. 15. The disrupted multi-scale parameters are inputted into the patient-specific multi-scale model 300 at 1435. Finally, at 1440, the multi-scale model 300 determines a phenotype prediction.

Figure 15:
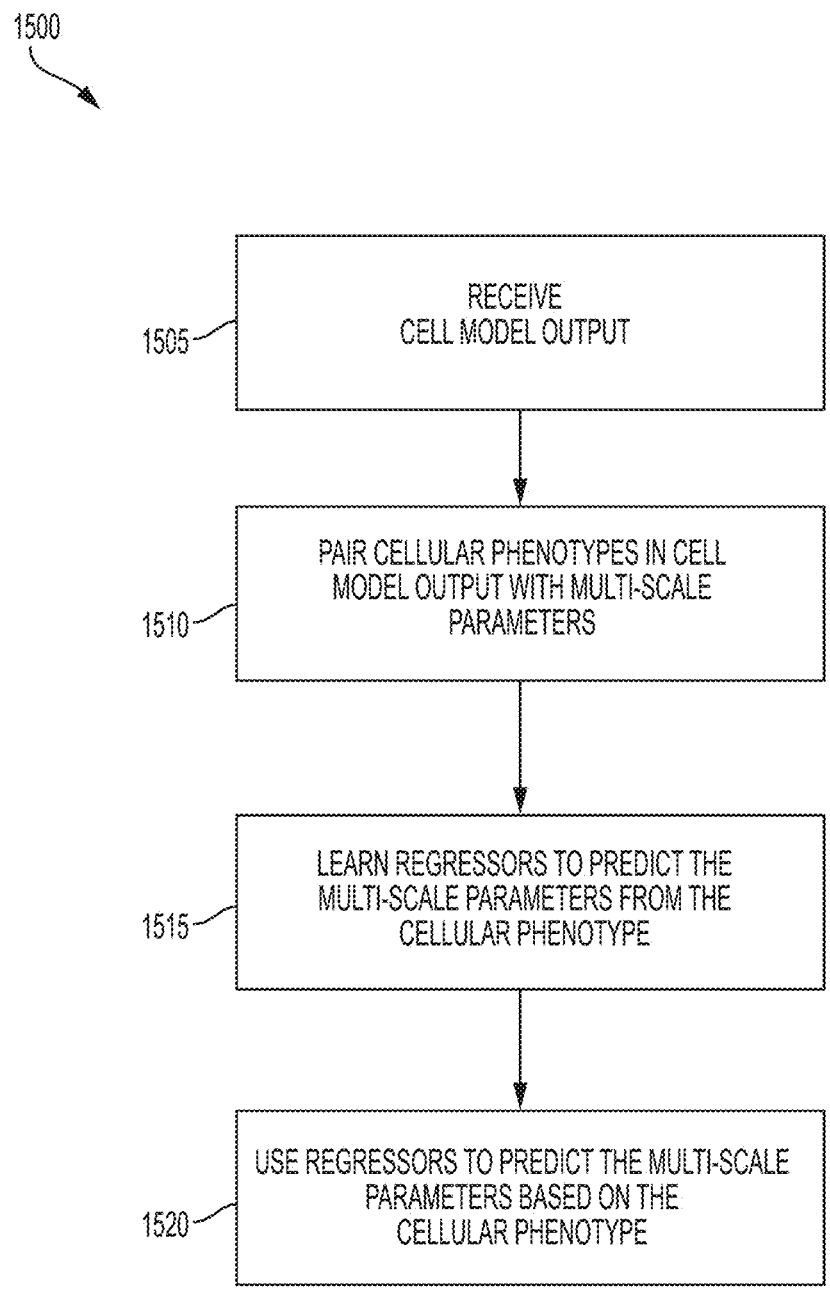
FIG. 15 provides an illustration of a process used by a cell model bridge included in a linking component when operating in bottom-up model, according to some embodiments of the present invention.

FIG. 15 provides an illustration of the process 1500 used by the cell model bridge 1120 included in the linking component 225 when operating in bottom-up model, according to some embodiments of the present invention. Given the patient-specific cell model 1115, whose parameters are defined according to the molecular findings returned by the molecular model 230, the cell model bridge 1120 estimates the parameters of the phenomenological models (e.g., cardiac electrophysiology model 505 and biomechanical model 510) such that the computed action potential and active stress match those computed with the cell model 1115.

Continuing with reference to FIG. 15, the process 1500 begins at 1505 as the cell model bridge 1120 receives output from the cell model 1115, including one or more cellular phenotypes. Next, at 1510, the cell model bridge 1120 pairs the received cellular phenotypes with the multi-scale parameters that, when processed by more simplified, phenomenological models (see, e.g., FIG. 5), result in the same phenotypes. To obtain the pairs, various approaches may be used. In some embodiments, a first approach is used, wherein a patient-specific procedure is available to create a database of paired items. In this approach, the multi-scale model parameters are estimated from the clinical and imaging data based on inverse method algorithms and the multi-scale model 300. For example, in the one embodiment, the cellular variables describe the action potential computed by a patient-specific TenTusscher model (cell model), while the multi-scale parameters are those of a phenomenological Mitchell-Schaeffer model. Similarly, the cellular variables may describe the stresses and kinetics computed by a Rice model, while the multi-scale parameters of a Chapelle model describe the strength of active force, active stiffness, and/or Z-disc stiffness. The resulting pairs are used to train the system. In other embodiments, a second, simulation-based approach is used, wherein the cell model 1115 and the multi-scale model 300 are used to compute various cellular phenotypes. The parameters yielding similar phenotypes are used as pairs to train the system. The system 100 may offer annotation and correction tools to manually update the pairs as needed.

At 1515, given the pairs of cellular phenotypes and multi-scale parameters, the system learns regressors to predict the multi-scale parameters from the cellular phenotype. To ensure statistical power and significance, advanced machine learning algorithms and manifold learning may be employed to estimate the regression model. For example, in one embodiment, non-linear manifold learning algorithms are utilized to reduce the dimensionality of the problem and cope with the high number of variables. Once the learning process is performed, at 1520, the regressors are used to predict the multi-scale parameters. As a result, the final model parameters are consistent with molecular data (as determined by the cell model output) and the clinical data (as determined by the multi-scale parameters).

In some embodiments, spatial information obtained from the images is used to estimate the multi-scale parameters locally. For example, the location of the may be used to weight the importance of the abnormal behavior predicted by the cell model in that region, while normal parameters are kept in visibly healthy regions. Finally, 3D atlases of protein/gene expression, if available, may also be employed to further constrain the search space and refine the localization of the identified molecular abnormalities.

The system 100 may produce new data that enhance a clinician decision-making process. For example, 3D maps of parameters computed using the bottom-up mode described herein (see FIG. 14) may be presented to the clinicians for spatial analysis (e.g. tissue strain, cross-bridge efficiency, action potential duration, etc.). These measurements may allow for further actions such as disease stratification (e.g. model-based genotype/phenotype classification), molecular data discrimination, and improved diagnosis. Additionally, because the measurements are 3D, the spatial distribution of disrupted molecular pathways can be analyzed in detail (e.g., within a scar). The system 100 is also generative and, thus, can predict phenotypic effects of molecular changes. Changes in molecular data may be entered into the system to generate new mapping to the multi-scale model and new multi-scale model parameters. As a result, the patient-specific model 300 can be updated later on during disease monitoring phase based on new molecular data to predict their phenotypic effects. The updated multi-scale model parameters can be used to quantitatively evaluate the disease progression. Furthermore, since spatial signatures of disrupted molecular pathways may be computed by the system 100, the aggressiveness of visible lesions can be studied at both molecular and phenotypic scales. Alternatively, the clinician can modify system parameters to mimic therapies (e.g., drugs, devices, etc.) and predict their outcome.

Figure 16:
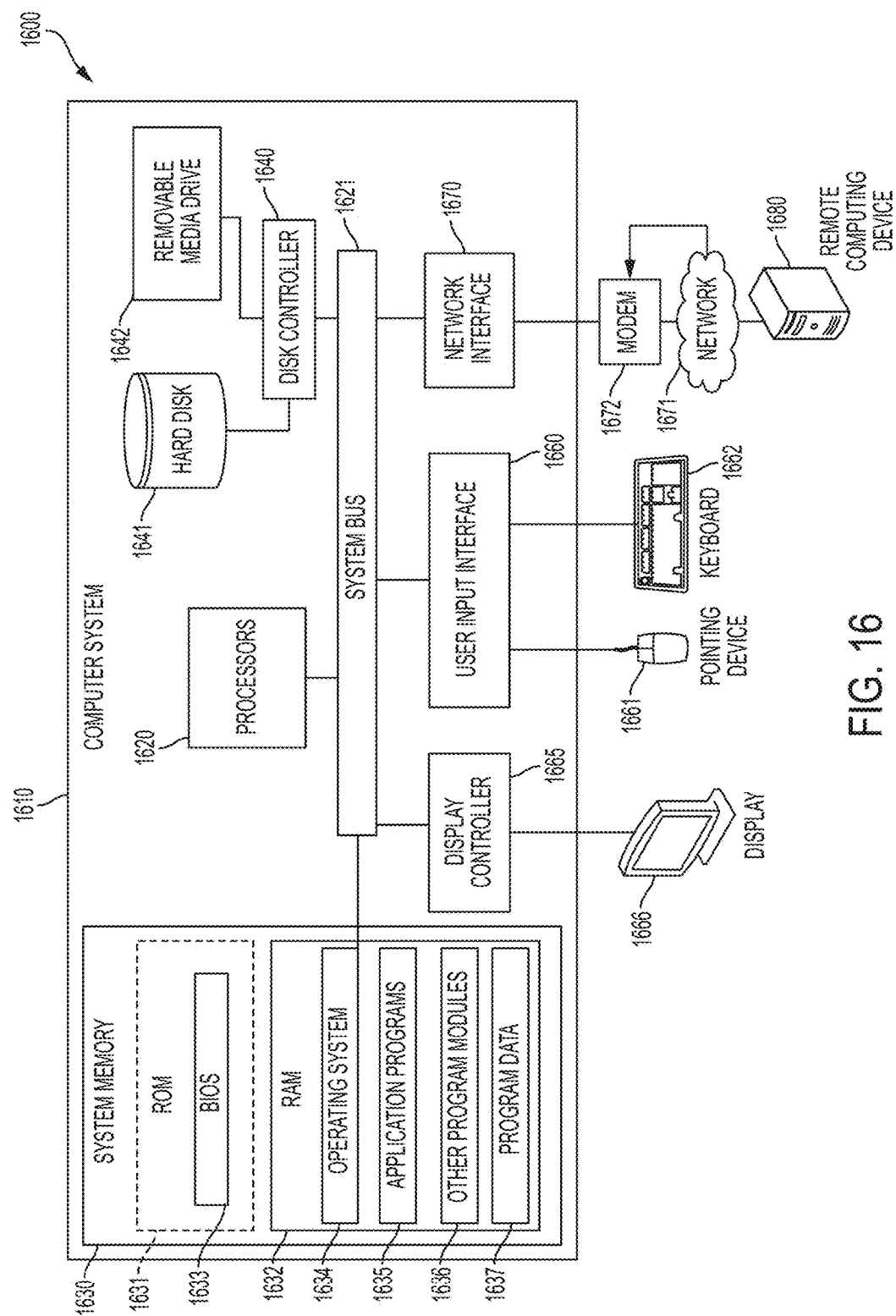
FIG. 16 illustrates an exemplary computing environment within which embodiments of the invention may be implemented.

FIG. 16 illustrates an exemplary computing environment 1600 within which embodiments of the invention may be implemented. Computing environment 100 may include computer system 1610, which is one example of a general purpose computing system upon which embodiments of the invention may be implemented. For example, in some embodiments, computer system 1610 is used to implement modeling computer 120. Computers and computing environments, such as computer 1610 and computing environment 1600, are known to those of skill in the art and thus are described briefly here.

As shown in FIG. 16, the computer system 1610 may include a communication mechanism such as a bus 1621 or other communication mechanism for communicating information within the computer system 1610. The system 1610 further includes one or more processors 1620 coupled with the bus 1621 for processing the information. The processors 1620 may include one or more central processing units (CPUs), graphical processing units (GPUs), or any other processor known in the art.

The computer system 1610 also includes a system memory 1630 coupled to the bus 1621 for storing information and instructions to be executed by processors 1620. The system memory 1630 may include computer readable storage media in the form of volatile and/or nonvolatile memory, such as read only memory (ROM) 1631 and/or random access memory (RAM) 1632. The system memory RAM 1632 may include other dynamic storage device(s) (e.g., dynamic RAM, static RAM, and synchronous DRAM). The system memory ROM 1631 may include other static storage device(s) (e.g., programmable ROM, erasable PROM, and electrically erasable PROM). In addition, the system memory 1630 may be used for storing temporary variables or other intermediate information during the execution of instructions by the processors 1620. A basic input/output system 1633 (BIOS) containing the basic routines that help to transfer information between elements within computer system 1610, such as during start-up, may be stored in ROM 1631. RAM 1632 may contain data and/or program modules that are immediately accessible to and/or presently being operated on by the processors 1620. System memory 1630 may additionally include, for example, operating system 1634, application programs 1635, other program modules 1636 and program data 1637.

The computer system 1610 also includes a disk controller 1640 coupled to the bus 1621 to control one or more storage devices for storing information and instructions, such as a magnetic hard disk 1641 and a removable media drive 1642 (e.g., floppy disk drive, compact disc drive, tape drive, and/or solid state drive). The storage devices may be added to the computer system 1610 using an appropriate device interface (e.g., a small computer system interface (SCSI), integrated device electronics (IDE), Universal Serial Bus (USB), or FireWire).

The computer system 1610 may also include a display controller 1665 coupled to the bus 1621 to control a display or monitor 1665, such as a cathode ray tube (CRT) or liquid crystal display (LCD), for displaying information to a computer user. The computer system includes an input interface 1660 and one or more input devices, such as a keyboard 1661 and a pointing device 1662, for interacting with a computer user and providing information to the processor 1620. The pointing device 1662, for example, may be a mouse, a trackball, or a pointing stick for communicating direction information and command selections to the processor 1620 and for controlling cursor movement on the display 1666. The display 1666 may provide a touch screen interface which allows input to supplement or replace the communication of direction information and command selections by the pointing device 1661.

The computer system 1610 may perform a portion or all of the processing steps of embodiments of the invention in response to the processors 1620 executing one or more sequences of one or more instructions contained in a memory, such as the system memory 1630. Such instructions may be read into the system memory 1630 from another computer readable medium, such as a hard disk 1641 or a removable media drive 1642. The hard disk 1641 may contain one or more datastores and data files used by embodiments of the present invention. Datastore contents and data files may be encrypted to improve security. The processors 1620 may also be employed in a multi-processing arrangement to execute the one or more sequences of instructions contained in system memory 1630. In alternative embodiments, hard-wired circuitry may be used in place of or in combination with software instructions. Thus, embodiments are not limited to any specific combination of hardware circuitry and software.

As stated above, the computer system 1610 may include at least one computer readable medium or memory for holding instructions programmed according embodiments of the invention and for containing data structures, tables, records, or other data described herein. The term "computer readable medium" as used herein refers to any medium that participates in providing instructions to the processor 1620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1641 or removable media drive 1642. Non-limiting examples of volatile media include dynamic memory, such as system memory 1630. Non-limiting examples of transmission media include coaxial cables, copper wire, and fiber optics, including the wires that make up the bus 1621. Transmission media may also take the form of acoustic or light waves, such as those generated during radio wave and infrared data communications.

The computing environment 1600 may further include the computer system 1620 operating in a networked environment using logical connections to one or more remote computers, such as remote computer 1680. Remote computer 1680 may be a personal computer (laptop or desktop), a mobile device, a server, a router, a network PC, a peer device or other common network node, and typically includes many or all of the elements described above relative to computer 1610. When used in a networking environment, computer 1610 may include modem 1672 for establishing communications over a network 1671, such as the Internet. Modem 1672 may be connected to system bus 1621 via user network interface 1670, or via another appropriate mechanism.

Network 1671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1610 and other computers (e.g., remote computing system 1680). The network 1671 may be wired, wireless or a combination thereof. Wired connections may be implemented using Ethernet, Universal Serial Bus (USB), RJ-16 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1671.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system operating in one of two modes, individually or in an iterative sequence, to provide an integrated analysis of molecular data, imaging data, and clinical data associated with a patient, the system comprising:
   a multi-scale organ model;
   a molecular model;
   one or more processors; and
   a non-transitory, computer-readable storage medium in operable communication with the processor, wherein the computer-readable storage medium contains one or more programming instructions that, when executed, cause the one or more processors to:
      perform a top-down process when the system is configured in a first mode, the top-down process comprising:
         executing the multi-scale organ model to generate one or more estimated multi-scale parameters by fitting a multi-scale phenomenological model of organ function to the clinical data and the imaging data using inverse problem algorithms, integrating the estimated multi-scale parameters with at least one of patient-specific information and disease subclass information to yield integrated phenotypic data, performing omics data analysis on molecular profile information to determine sequence variant data and differential expression data, executing the molecular model to perform molecular network analysis based on the integrated phenotypic data, the sequence variant data, and the differential expression data to identify one or more of disrupted molecular pathways, relevant biomarkers to a disease, and regulatory mechanisms causing a disease-related phenotype, and perform a bottom-up process when the system is configured in a second mode, the bottom-up process comprising:

performing omics data analysis on molecular profile information to determine sequence variant data and differential expression data, executing the molecular model to perform molecular network analysis based on the sequence variant data, and the differential expression data to identify one or more disrupted cellular model parameters, applying a patient-specific cell model to the disrupted cellular model parameters to identify output values indicative of kinetic and electrophysiological effects of molecular changes on cell function, applying a machine learning algorithm to identify one or more disrupted multi-scale parameters based on the output values, and executing the multi-scale organ model using the disrupted multi-scale parameters to yield a phenotype prediction.

2. The system of claim 1, wherein the patient-specific cell model comprises:

an ion interaction model of cardiac electrophysiology configured to determine one or more indicators of the electrophysiological activity within a cell; and an electromechanical coupling model configured to determine one or more indicators of patient-specific cell active force and one or more indicators of passive stress based on the indicators of electrophysiological activity within the cell.

3. The system of claim 1, wherein the system further comprises:

a database of paired items, each paired item associating one or more known multi-scale parameters with one or more known values indicative of the kinetic and electrophysiological effects of molecular changes on cell function, wherein the disrupted multi-scale parameters are generated based on the values indicative of the kinetic and electrophysiological effects of molecular changes on cell function by applying the machine learning algorithm to the database of paired items.

4. A computer-based method for performing an integrated analysis of molecular data, imaging data, and clinical data from a patient, the method comprising:

performing, by one or more computers, an omics data analysis on molecular profile information and thereby determining sequence variant data and differential expression data;

executing, by the one or more computers, a molecular model and thereby performing molecular network analysis based on the sequence variant data, and the differential expression data to identify one or more disrupted cellular model parameters;

computing, by the one or more computers, one or more values indicative of kinetic and electrophysiological effects of molecular changes on cell function based on the disrupted cellular model parameters;

generating, by the one or more computers, one or more disrupted multi-scale parameters by applying a machine learning algorithm to the values indicative of the kinetic and electrophysiological effects of molecular changes on cell function by:

creating a database of paired items, each paired item associating one or more known multi-scale parameters with one or more values indicative of the kinetic and electrophysiological effects of molecular changes on cell function, training the machine learning algorithm using the database of paired items; and applying the machine learning algorithm to the database of paired items to compute the disrupted multi-scale parameters based on the output values indicative of the kinetic and electrophysiological effects of molecular changes on cell function; and utilizing a patient-specific multi-scale model and thereby determining a phenotype prediction for the disease based on the disrupted multi-scale parameters.

5. The method of claim 4, wherein computing the values indicative of the kinetic and electrophysiological effects of molecular changes on cell function comprises:

determining an indicator of electrophysiological activity within the patient;

determining a patient-specific cell active stress indicator and patient-specific cell passive stress indicator; and computing the output values indicative of the kinetic and electrophysiological effects of molecular changes on cell function based on the indicator of electrophysiological activity within the patient, the patient-specific cell active stress indicator, and the patient-specific cell passive stress indicator.

6. The method of claim 4, wherein the machine learning algorithm is constrained based on the clinical data associated with the patient.

7. The method of claim 4, further comprising:

storing a new paired item in the database of paired items, the new paired item associating the disrupted multi-scale parameters and the values indicative of the kinetic and electrophysiological effects of molecular changes on cell function.

8. The method of claim 4, wherein creating the database of paired items comprises:

for each of a plurality of patients, storing a first paired item in the database of paired items, the first paired item indicating an association between first multi-scale parameters and first values indicative of the kinetic and electrophysiological effects of molecular changes on cell function associated with a respective patient.

9. The method of claim 4, wherein creating the database of paired items comprises:

utilizing a generalized multi-scale model to determine a plurality of first cellular phenotypes, each first cellular phenotype corresponding to distinct multi-scale parameters;

utilizing a cellular model to determine a plurality of second cellular phenotypes, each second cellular phenotype corresponding to distinct cellular model parameters; and for each first cellular phenotype that is equivalent to a second cellular phenotype, storing a first paired item in the database of paired items, the first paired item indicating an association between respective multi-scale parameters and respective cellular model parameters.

10. The method of claim 4, wherein the output values indicative of the kinetic and electrophysiological effects of molecular changes on cell function comprise one or more of an action potential shape, an indication of timing associated with an action potential, an indication of strength of cell active stress and an indication of stiffness of a cellular and an extra-cellular matrix.

11. The method of claim 4, wherein computing the values indicative of the kinetic and electrophysiological effects of molecular changes on cell function based on the disrupted cellular model parameters comprises:

determining, by an ion interaction model of cardiac electrophysiology, one or more indicators of the electrophysiological activity within a cell; and determining, by an electromechanical coupling model, patient-specific indicators of cell active stress and indicators of passive stress based on the indicators of electrophysiological activity.

* * * * *